(12) United States Patent
Skelton

(10) Patent No.: US 8,150,531 B2
(45) Date of Patent: Apr. 3, 2012

(54) ASSOCIATING THERAPY ADJUSTMENTS WITH PATIENT POSTURE STATES

(75) Inventor: Dennis M. Skelton, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 219 days.

(21) Appl. No.: 12/433,520

(22) Filed: Apr. 30, 2009

(65) Prior Publication Data

US 2010/0010432 A1   Jan. 14, 2010

Related U.S. Application Data

(60) Provisional application No. 61/080,002, filed on Jul. 11, 2008.

(51) Int. Cl.
*A61N 1/08* (2006.01)
(52) U.S. Cl. .......................................................... 607/62
(58) Field of Classification Search .............. 607/45–46, 607/60–62, 115–118
See application file for complete search history.

(56) References Cited

U.S. PATENT DOCUMENTS

| | | | |
|---|---|---|---|
| 4,297,685 A | 10/1981 | Brainard, II | |
| 4,365,633 A | 12/1982 | Loughman | |
| 4,543,955 A | 10/1985 | Schroeppel | |
| 4,550,736 A | 11/1985 | Broughton et al. | |
| 4,566,456 A | 1/1986 | Koning et al. | |
| 4,771,780 A | 9/1988 | Sholder | |
| 4,776,345 A | 10/1988 | Cohen et al. | |
| 4,846,180 A | 7/1989 | Buffet | |
| 4,846,195 A | 7/1989 | Alt | |
| 5,031,618 A | 7/1991 | Mullett | |
| 5,040,534 A | 8/1991 | Mann et al. | |
| 5,040,536 A | 8/1991 | Riff | |
| 5,058,584 A | 10/1991 | Bourgeois | |
| 5,125,412 A | 6/1992 | Thornton | |
| 5,154,180 A | 10/1992 | Blanchet et al. | |
| 5,158,078 A | 10/1992 | Bennett et al. | |
| 5,167,229 A | 12/1992 | Peckham et al. | |

(Continued)

FOREIGN PATENT DOCUMENTS

DE   19831109   1/2000

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Carl H Layno
*Assistant Examiner* — Paula J Stice
(74) *Attorney, Agent, or Firm* — Shumaker & Sieffert, P.A.

(57) ABSTRACT

A therapy adjustment received from a patient is associated with a sensed patient posture state. Thereafter, a stability indication can be associated with the sensed posture state to indicate that a therapy adjustment specific to the sensed posture state was received and implemented. In addition, therapy parameter values associated with related patient posture states are updated based on the therapy adjustment. In some examples, only the related posture states that are not associated with respective stability indications are updated based on the therapy adjustment. The absence of a stability indication indicates that the patient has not inputted a therapy adjustment specific to the respective related posture state. As a result, the therapy parameter values associated with the related posture states that are not associated with stability indications may float until the patient adjusts the therapy parameter value associated with the respective related posture state.

37 Claims, 20 Drawing Sheets

U.S. PATENT DOCUMENTS

| | | | |
|---|---|---|---|
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al. |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |

| Patent/Pub No. | Date | Inventor |
|---|---|---|
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann et al. |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/1050026 | 6/2007 | Bourget |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |

| | | |
|---|---|---|
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| DE | 10024103 | 11/2001 |
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

"IBM and Citizen Watch develop Linux-Based WatchPad," http://wwwlinuxdevices.com/news/NS6580187845.html, 5 pp., 2006.

"MiniMitter® Physiological and Behavioral Monitoring for Humans and Animals," http://www.minimitter.com/Products/ Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-51, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.

Dinner, "Effect of Sleep on Epilepsy," Journal of Clinical Neurophysiology, American Clinical Neurophysiology Society, 19(6), pp. 504-513, 2002.

Foerster et al., "Motion Pattern and Posture: Correctly Assessed by Calibrated Accelerometers," Forschungsgrupe Psychophysiologie, Universität Freiburg, Germany, Mar. 2000, 28 pp.

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.

Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.

Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.

Goodrich et al., "The Prediction of Pain Using Measures of Sleep Quality," Pain Digest, 8:23-25, 1998.

Heinz et al., "Using Wearable Sensors for Real-time Recognition Tasks in Games of Martial Arts—An Initial Experiment," Institute for Computer Systems and Networks (CSN), UMIT- University of Health Systems, Medical Informatics and Technology Hall in Tyrol, Austria, 2006, 5 pp., http://eis.comp.lancs.ac.uk/fileadmin/relate/publication/2006-WearableSensors.pdf.

Hendelman et al., "Validity of Accelerometry for the Assessment of Moderate Intensity Physical Activity in the Field," Medicine & Science in Sports & Exercise, pp. S442-S449, 2000.

Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.

Husak, "Model of Tilt Sensor Systems, "ICECS 2002, $9^{th}$ IEEE International Conference on Electronics, Circuits and Systems, vol. 1, pp. 227-230, 2002.

Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.

Kassam, "2005 EDP Topic "MK4": Tremor Data-Logger for Parkinson's Disease Patients," http://www.ee.ryerson.ca/~courses/edp2005/MK4.html, 3 pp., 2005.

Kerr et al., "Analysis of the sit-stand-sit movement cycle in normal subjects," Clinical Biomechanics, vol. 12, No. 4, pp. 236-245, 1977.

Kiani et al., "Computerized Analysis of Daily Life Motor Activity for Ambulatory Monitoring," Technology and Health Care 5, pp. 307-318, 1997.

Kitchin et al., "Compensating for the 0 g Offset Drift of the ADXL50 Accelerometer," Analog Devices Application Note AN-380, 2 pp.

Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.

Leiper et al., "Sensory Feedback for Head Control in Cerebral Palsy," Physical Therapy, vol. 61, No. 4, pp. 512-518, Apr. 1981.

Lorussi, "Wearable, Redundant Fabric-Based Sensor Arrays for Reconstruction of Body Segment Posture," IEEE Sensors Journal, vol. 4, No. 6, pp. 808-817, Dec. 2004.

Mathie et al., "A Pilot Study of Long-Term Monitoring of Human Movements in the Home Using Accelerometer," Journal of Telemedicine and Telecare10:144-151, Jun. 2007.

Mathie et al., "Determining Activity Using a Triaxial Accelerometer," Proceedings of the Second Joint EMBS/BMES Conference, Houston, TX, pp. 2481-2482, Oct. 23-26, 2002.

Mattmann et al., "Recognizing Upper Body Postures Using Textile Strain Sensors," Proceedings Eleventh IEEE International Symposium on Wearable Computers, ISWC, pp. 29-36, 2007.

Mendez et al., "Interactions Between Sleep and Epilepsy," Journal of Clinical Neurophysiology, American Clinical Neurophysiology Society, 18(2), pp. 106-127, 2001.

Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.

Slyper et al., "Action Capture with Accelerometers," Eurographics/ ACM SIGGRAPH Symposium on Computer Animation, Carnegie Mellon University, 7 pp., 2008.

Smith et al., "How do sleep disturbance and chronic pain inter-relate? Insights from the longitudinal and cognitive-behavioral clinical trials literature," Sleep Medicine Reviews, YSMRV 286, pp. 1-14, 2003.

Smith et al., "Presleep cognitions in Patients with Insomnia Secondary to Chronic Pain," Journal of Behavioral Medicine, vol. 24, No. 1, pp. 93-114, 2001.

Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.

Trolier-Mckinstry et al., "Thin Film Piezoelectrics for MEMS," Journal of Electroceramics, v. 12, No. 1-2, pp. 7-17, Jan./Mar. 2004.

Tuck, "Implementing Auto-Zero Calibration Technique for Accelerometers," Freescale Semiconductor Application Note AN3447, 5 pp., Mar. 2007.

Tuisku, "Motor Activity Measured by Actometry in Neuropsychiatric Disorders," Department of Psychiatry, University of Helsinki, Helsinki, Finland, 115 pp., 2002.

Vega-Gonzalez, "Upper Limb Activity Monitoring," Arch Phys Med Rehabil, vol. 86, pp. 541-548, Mar. 2005.

Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.

PCT/US2009/48999, International Search Report and Written Opinion dated Sep. 22, 2009, 6 pp.

U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/433,442, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.

Office Action dated Oct. 6, 2011 for U.S. Appl. No. 12/433,756, (6 pages).

Office Action dated Oct. 14, 2011 for U.S. Appl. No. 12/433,808, (9 pages).

Responsive Amendment dated Dec. 28, 2011 for U.S. Appl. No. 12/433,756, (14 pages).

Response dated Jan. 12, 2012 for U.S. Appl. No. 12/433,808, (8 pages).

POSTURE STATE GROUP A — 310

| POSTURE STATE | STABILITY INDICATION | THERAPY PARAMETER VALUE |
|---|---|---|
| LYING FRONT | 1 | 2.2 V |
| LYING BACK | 0 | 2.2 V |
| LYING LEFT | 0 | 2.2 V |
| LYING RIGHT | 0 | 2.2 V |

FIG. 19A

POSTURE STATE GROUP A — 310

| POSTURE STATE | STABILITY INDICATION | THERAPY PARAMETER VALUE |
|---|---|---|
| LYING FRONT | 1 | 2.2 V |
| LYING BACK | 1 | 3.8 V |
| LYING LEFT | 0 | 2.2 V |
| LYING RIGHT | 0 | 2.2 V |

FIG. 19B

POSTURE STATE GROUP A — 310

| POSTURE STATE | STABILITY INDICATION | THERAPY PARAMETER VALUE |
|---|---|---|
| LYING FRONT | 1 | 2.2 V |
| LYING BACK | 1 | 3.8 V |
| LYING LEFT | 0 | 2.1 V |
| LYING RIGHT | 1 | 2.1 V |

FIG. 19C

ASSOCIATING THERAPY ADJUSTMENTS WITH PATIENT POSTURE STATES

This application claims the benefit of U.S. Provisional Application No. 61/080,002 to Skelton et al., entitled, "POSTURE STATE DATA COLLECTION AND ASSOCIATED PROGRAMMING" and filed on Jul. 11, 2008, the entire content of which is incorporated herein by reference.

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient may be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure describes techniques for associating a detected therapy adjustment with one or more posture states. A therapy system stores a plurality of patient posture states and associates each patient posture state with at least one therapy parameter value. During the course of therapy delivery by the therapy system, a patient may make an adjustment to the therapy parameter value applicable to the posture state. In accordance with techniques described herein, the therapy system associates the adjusted therapy parameter value with a sensed patient posture state.

In some examples, the therapy system determines the posture state with which the patient intended the therapy adjustment to be associated through implementation of a posture stability timer, and, in some cases, a posture search timer, which track therapy adjustments and posture state changes in real time. After receiving a therapy adjustment and associating the therapy adjustment with a sensed posture state, a stability indication can be associated with the sensed posture state to indicate that a therapy adjustment specific to the sensed posture state was received and implemented.

In addition to associating the therapy adjustment with a sensed patient posture state, therapy parameter values associated with related patient posture states are updated based on the therapy adjustment. In some examples, only the related patient posture states that are not associated with respective stability indications are updated based on the therapy adjustment. The absence of a stability indication indicates that the patient has not inputted a therapy adjustment specific to the respective related posture state. As a result, the therapy parameter values associated with the related posture states that are not associated with stability indications "float" until the patient adjusts the therapy parameter value associated with the respective related posture state. The therapy parameter values may "float" in the sense that they are not fixed and vary based on therapy adjustments provided by the patient for at least one related posture state.

In one example, the disclosure is directed to a method comprising receiving user input indicating an adjustment to a first therapy parameter value that defines therapy delivered to a patient, associating the adjustment with a sensed posture state of the patient, and, based on the adjustment, updating a second therapy parameter value associated with at least one patient posture state related to the sensed posture state and not associated with a respective stability indication.

In another example, the disclosure is directed to a system comprising a posture state sensor that generates a signal indicative of a patient posture state, a user input mechanism that receives user input indicating an adjustment to a first therapy parameter value that defines therapy delivered to a patient, and a processor that associates the adjustment with a sensed posture state of the patient determined based on the signal from the posture state sensor, and based on the adjustment, updates a second therapy parameter value associated with at least one patient posture state related to the sensed posture state and not associated with a respective stability indication.

In another example, the disclosure is directed to a system comprising means for receiving user input indicating an adjustment to a first therapy parameter value that defines therapy delivered to a patient, means for associating the adjustment with a sensed posture state of the patient, and means for updating a second therapy parameter value associated with at least one patient posture state related to the sensed posture state and not associated with a respective stability indication based on the adjustment.

In another example, the disclosure is directed to a computer-readable medium comprising instructions. The instructions cause a programmable processor to receive user input indicating an adjustment to a first therapy parameter value that defines therapy delivered to a patient, associate the adjustment with a sensed posture state of the patient, based on the adjustment, update a second therapy parameter value associated with at least one patient posture state related to the sensed posture state and not associated with a respective stability indication, and control a medical device to deliver therapy to the patient according to the adjusted first therapy parameter value and the updated second therapy parameter value.

In another example, the disclosure is directed to a system comprising means for receiving user input indicating an adjustment to a first therapy parameter value that defines therapy delivered to a patient, means for associating the adjustment with a sensed posture state of the patient, and means for updating a second therapy parameter value associated with at least one patient posture state related to the sensed posture state and not associated with a respective stability indication based on the adjustment.

In another example, the disclosure is directed to a computer-readable medium comprising instructions. The instructions cause a programmable processor to perform any of the techniques described herein. The instructions may be encoded in the computer-readable medium. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

The details of one or more examples of systems, devices, and techniques are set forth in the accompanying drawings and the description below. Other features, objects, and advantages of the disclosure will be apparent from the description and drawings, and from the claims.

BRIEF DESCRIPTION OF THE DRAWINGS

FIGS. 19A-19C illustrate an example data structure that associates posture states with therapy parameter values and stability indications.

DETAILED DESCRIPTION

Figure 1A:
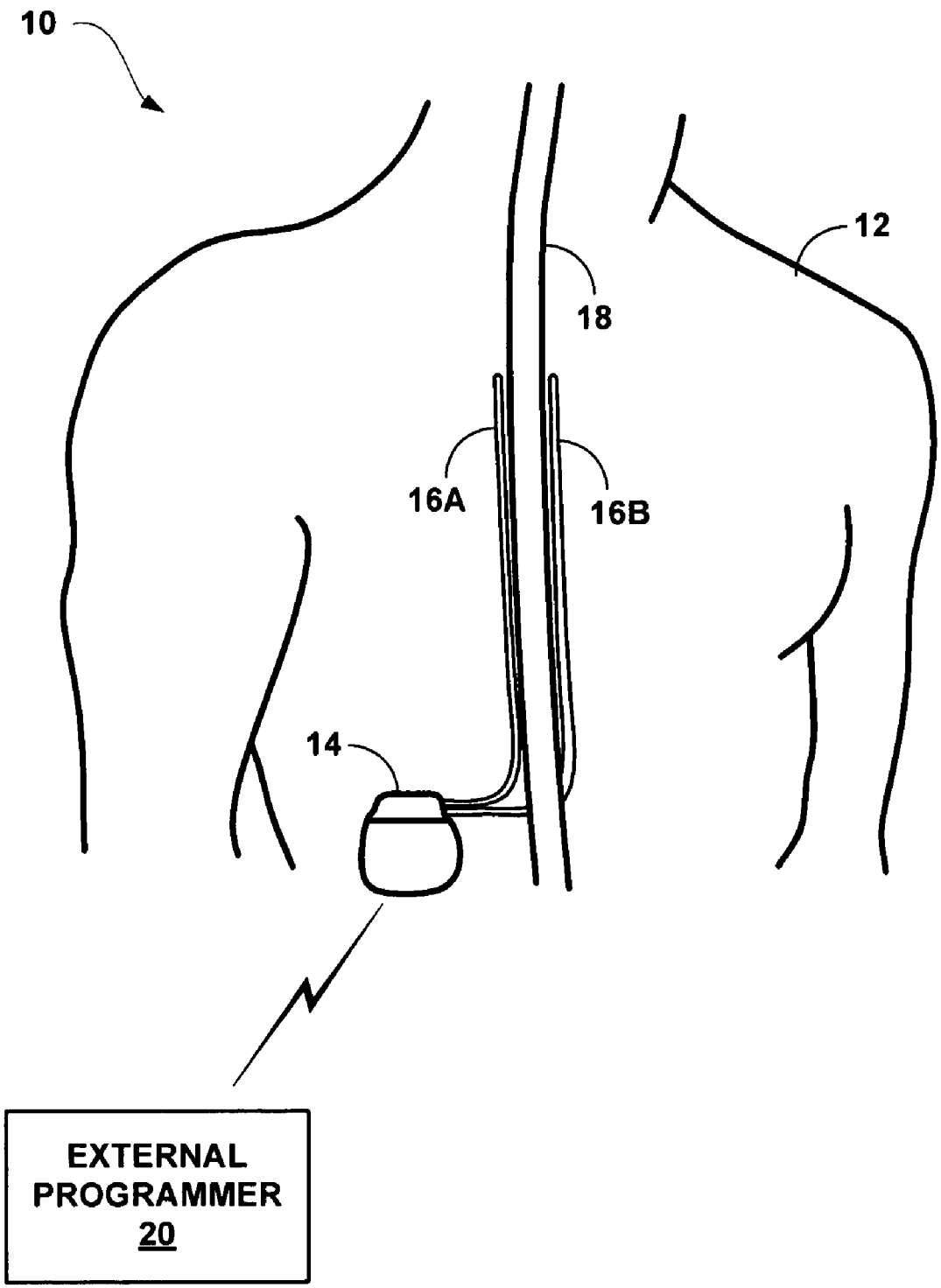
FIG. 1A is a conceptual diagram illustrating an example implantable therapy system including a medical device and two implantable stimulation leads.

In some medical devices (e.g., medical devices that deliver electrical stimulation therapy or deliver a therapeutic agent), therapeutic efficacy may change as the patient changes posture states. In general, a posture state refers to a patient posture or a combination of posture and activity. For example, an upright posture state may be sub-categorized as upright and active or upright and inactive. Other posture states, such as lying down posture states, may or may not have an activity component. Efficacy may refer, in general, to a combination of complete or partial alleviation of symptoms alone, or in combination with a degree of undesirable side effects.

Changes in posture state may cause changes in efficacy due to changes in distances between electrodes or other therapy delivery elements, e.g., due to temporary migration of leads or catheters caused by forces or stresses associated with different postures, or from changes in compression of patient tissue in different posture states. In addition, posture state changes may present changes in symptoms or symptom levels, e.g., pain level. To maintain therapeutic efficacy, it may be desirable to adjust one or more therapy parameter values based on different postures and/or activities engaged in by the patient. A medical device may adjust therapy by modifying values for one or more therapy parameters, e.g., by specifying adjustments to a specific therapy parameter or by selecting different therapy programs or groups of programs that define different sets of therapy parameter values. That is, a therapy adjustment may be accomplished by selecting or adjusting parameter values for a current program (including parameters such as amplitude, pulse width, pulse rate, electrode combination, electrode polarity) or by selecting a different therapy program.

A change in efficacy due to changes in posture state may require the patient to continually manage therapy by manually adjusting certain therapy parameters, such as amplitude, pulse rate, or pulse width, or selecting different therapy programs to achieve more efficacious therapy throughout many different posture states. In some cases, a medical device may employ a posture state module including a posture state sensor (e.g., an accelerometer or a piezoelectric sensor) that generates a signal indicative of the patient posture state. The medical device may adjust therapy parameters in response to a posture state determined based on the output from the posture state module. Therapy adjustments in response to different posture states may be fully automatic, semi-automatic in the sense that a user may provide approval of proposed changes, or user-directed in the sense that the patient may manually adjust therapy based on the posture state indication.

Therapy may be provided to a patient in order to relieve symptoms from any number of conditions and diseases. An implantable medical device (IMD) that delivers stimulation therapy, therapeutic agent delivery or another type of therapy may also employ a posture state sensor that senses the posture state in which the patient is currently engaged. As described in further detail below, the sensed posture state is associated with user (e.g., a patient or clinician) adjustments to one or more therapy parameter values made during the sensed posture state or prior to the patient assuming the sensed posture state. The therapy adjustment is associated with the sensed posture state in a memory of the IMD or another device, such as a programmer. In addition, upon associating the therapy adjustment with the sensed posture state in the memory, a stability indication is associated with the sensed posture state in the memory. The stability indication indicates that the patient provided a therapy adjustment that was specific to the associated posture state.

As described in further detail below, the therapy adjustment may also be associated with at least one posture state related to the sensed posture state in the memory. Posture states may be considered to be related based on various factors, including similarity of patient symptoms when the patient occupies the posture states, similarity in therapy parameter values that provide efficacious therapy to the patient when the patient occupies the posture states, similarity of posture sensor outputs that indicate the posture states, and other factors considered by the clinician and/or the medical device.

In some examples, the related posture states with which the therapy adjustment is associated include related posture states that are not associated with stability indications. The therapy parameter values associated with the related posture states not including respective stability indications may be updated based on the therapy adjustment. A user may later review the associations of therapy adjustments and posture states and, if desired, modify therapy parameters to better treat the patient based on the associations.

FIG. 1A is a schematic diagram illustrating an implantable stimulation system 10 including a pair of implantable electrode arrays in the form of stimulation leads 16A and 16B. Although the techniques described in this disclosure may be generally applicable to a variety of medical devices including external and IMDs, application of such techniques to IMDs and, more particularly, implantable electrical stimulators (e.g., neurostimulators) will be described for purposes of illustration. More particularly, the disclosure will refer to an implantable spinal cord stimulation (SCS) system for purposes of illustration, but without limitation as to other types of medical devices.

As shown in FIG. 1A, system 10 includes an IMD 14 and external programmer 20 shown in conjunction with a patient 12, who is ordinarily a human patient. In the example of FIG. 1A, IMD 14 is an implantable electrical stimulator configured for spinal cord stimulation (SCS), e.g., for relief of chronic pain or other symptoms. Again, although FIG. 1A shows an implantable medical device, other examples may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat movement disorders (e.g., tremor), Parkinson's disease, epilepsy, urinary or fecal incontinence, sexual dysfunction, obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), pelvic floor stimulation, gastric stimulation, or any other stimulation therapy.

Each of leads 16 may include electrodes (not shown in FIG. 1A), and the parameters for a therapy program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms, such as continuous waveforms. Programs that control delivery of other therapies by IMD 14 may include other parameters, e.g., such as dosage amount, rate, or the like for drug delivery.

In the example of FIG. 1A, leads 16 carry one or more electrodes (not shown) that are placed adjacent to the target tissue of spinal cord 18 of patient 12. One or more electrodes may be disposed proximate to a distal end of a lead 16 and/or at other positions at intermediate points along the lead 16. Electrodes of leads 16 transfer electrical stimulation generated by IMD 14 to tissue of patient 12. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Leads 16 may be implanted within patient 12 and directly or indirectly (e.g., via a lead extension) electrically connected to IMD 14. Alternatively, as mentioned above, leads 16 may be implanted and coupled to an external stimulator, e.g., through a percutaneous port. In some cases, an external stimulator may be a trial or screening stimulation that used on a temporary basis to evaluate potential efficacy to aid in consideration of chronic implantation for a patient. In other examples, IMD 14 is a leadless stimulator with one or more arrays of electrodes arranged on a housing of the stimulator rather than leads that extend from the housing.

IMD 14 delivers electrical stimulation therapy to patient 12 via selected combinations of electrodes carried by one or both of leads 16. The target tissue for the electrical stimulation therapy may be any tissue affected by electrical stimulation energy, which may be in the form of electrical stimulation pulses or continuous waveforms. In some examples, the target tissue includes nerves, smooth muscle or skeletal muscle. In the example illustrated by FIG. 1A, the target tissue is tissue proximate spinal cord 18, such as within an intrathecal space or epidural space of spinal cord 18, or, in some examples, adjacent nerves that branch off of spinal cord 18. Leads 16 may be introduced into spinal cord 18 in via any suitable region, such as the thoracic, cervical or lumbar regions. Stimulation of spinal cord 18 may, for example, prevent pain signals from traveling through spinal cord 18 and to the brain of patient 12. Patient 12 may perceive the interruption of pain signals as a reduction in pain and, therefore, efficacious therapy results.

The deployment of electrodes via leads 16 connected to IMD 14 is described for purposes of illustration, but arrays of electrodes may be deployed in different ways. For example, a housing associated with a leadless stimulator may carry arrays of electrodes, e.g., rows and/or columns (or other patterns). Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to spinal cord 18 to reduce the amount of pain perceived by patient 12. As described above, IMD 14 may be used with a variety of different therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 generates and delivers electrical stimulation to patient 12 according to one or more therapy programs. A therapy program defines values for one or more therapy parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, wherein multiple programs are contained within each of a plurality of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 between different posture states may affect the ability of IMD 14 to deliver consistent efficacious therapy. For example, posture state changes may present changes in symptoms or symptom levels, e.g., pain level. As another example, a patient posture state may affect the relative location between the electrodes of leads 16 and a target therapy site. For example, leads 16 may migrate toward IMD 14 when patient 12 bends at the waist, resulting in displacement of electrodes relative to the target stimulation site and possible disruption in delivery of effective therapy. Stimulation energy transferred to target tissue may be reduced due to electrode migration, which may reduce therapeutic efficacy in terms of relief of symptoms (e.g., pain) or an increase in undesirable side effects.

As another example of how posture state may affect the relative location between the electrodes of leads 16 and a target therapy site, leads 16 may be compressed towards spinal cord 18 when patient 12 lies down. Such compression may cause an increase in the amount of stimulation energy transferred to the target stimulation site. An increase in stimulation energy transferred to the target stimulation site may cause unusual sensations or an otherwise undesirable intensity of therapy, which may both be considered undesirable side effects that undermine overall efficacy. Thus, in some examples, the amplitude of stimulation therapy may need to be decreased when patient 12 is lying down to mitigate additional pain or unusual sensations from the increased compression near electrodes of leads 16.

IMD 14 includes a posture state module that determines a patient posture state and, in some cases, a patient activity level. The patient posture and activity level may generally be referred to as a posture state. Example posture states may include "Upright," "Upright and Active," "Lying Back," "Lying Front," and so forth. IMD 14 includes a posture responsive therapy mode that, when activated, results in adjustment of one or more stimulation parameter values based on a detected posture state. The posture responsive therapy may help mitigate changes in the efficacy of therapy attributable to patient posture changes. For example, the posture state module may include one or more accelerometers that detect when patient 12 occupies a posture state for which it is appropriate to decrease the stimulation amplitude, e.g., when patient 12 lies down. IMD 14 may automatically reduce stimulation amplitude upon detecting patient 12 is lying down, thereby eliminating the need for patient 12 to manually adjust the therapy, which may be cumbersome.

Automatic adjustment of stimulation parameters based on a detected patient posture may also provide more responsive therapy because IMD 14 may detect a change in patient posture and modify therapy parameters faster than patient 12 manually modifying the therapy parameters. In some cases, however, patient 12 may manually modify one or more therapy parameter values. As described in further detail below, patient 12 may input a therapy adjustment into programmer 20 to adjust one or more therapy parameter values if, for example, patient 12 perceives the stimulation therapy as being too intense or not intense enough. Intensity may be a function of various stimulation parameters, such as a current or voltage amplitude of the stimulation signal, or the frequency or duty cycle of the stimulation signal.

In some examples, IMD 14 is configured to automatically decrease stimulation amplitude when it detects that patient 12 has changed posture states to a lying down state. The amplitude adjustment may be configured to be decreased at a rate suitable to prevent undesirable effects, e.g., such as the effects due to the compression of leads 16 towards spinal cord 18 when patient lies down. In some examples, IMD 14 is configured to decrease the stimulation amplitude to a suitable amplitude value substantially immediately upon detection by IMD 14 that patient 12 is lying down. In other examples, the stimulation amplitude may not be decreased substantially immediately by IMD 14 upon detection of patient 12 lying down, but instead IMD 14 may decrease the stimulation amplitude to a suitable amplitude level at a rate of changes that is suitable to prevent patient 12 from experiencing undesirable stimulation effects, e.g., due to increased transfer of stimulation energy to tissue of patient 12. In some examples, IMD 14 may substantially instantaneously decrease the stimulation amplitude to a suitable amplitude value when IMD detects that patient 12 is lying down.

Many other examples of reduced efficacy due to increase coupling or decreased coupling of stimulation energy to target tissue may occur due to changes in posture and/or activity level associated with patient posture state. To avoid or reduce possible disruptions in effective therapy due to posture state changes, IMD 14 may include a posture state module that detects the posture state of patient 12 and causes the IMD 14 to automatically adjust stimulation according to the detected posture state. For example, a posture state module may include an activity sensor such as an accelerometer that detects when patient 12 lies down, stands up, or otherwise changes posture.

In response to a posture state indication by the posture state module, IMD 14 may change program group, program, stimulation amplitude, pulse width, pulse rate, and/or one or more other parameters, groups or programs to maintain therapeutic efficacy. When patient 12 lies down, for example, IMD 14 may automatically reduce stimulation amplitude so that patient 12 does not need to reduce stimulation amplitude manually. In some cases, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

A user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy modifications relating to changes in the posture state of patient 12. As another example, a user may select therapy programs or program groups and associate the programs or groups with patient posture states in a memory of programmer 20 and/or IMD 14. Again, a therapy program may be characterized by an electrode combination, electrode polarities, voltage or current amplitude, pulse width, pulse rate, and/or duration. A group may be characterized by multiple programs that are delivered simultaneously or on an interleaved or rotating basis. Programmer 20 transmits the commands, programs or other information to IMD 14 with the aid of wireless communication signals.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use.

During a programming session, which may take place prior to initiation of chronic therapy delivery by IMD 14, a clinician can select initial values for therapy parameters associated with each of a plurality of posture states. For each of the plurality of posture states, the initial therapy parameter values provide efficacious therapy to patient 12 when patient 12 occupies the respective posture state. The initial therapy parameter values may be determined in a clinic. IMD 14 is programmed to automatically select therapy parameter values that define therapy delivery to patient 12 based on a posture state sensed via the posture state module of IMD 14. In this way, IMD 14 provides posture responsive therapy to patient 12.

After the selection of initial therapy parameter values and during the delivery of trial (e.g., temporary) or chronic (e.g., indefinite and not temporary) stimulation therapy by IMD 14, patient 12 may make therapy adjustments to customize the therapy parameter values. Patient 12 may make therapy adjustments either after patient 12 transitions to a posture state or in anticipation of the next posture state. IMD 14 includes a record mode in which IMD 14 stores all therapy adjustments inputted by the user with a specific posture state. In examples in which IMD 14 is in a record mode, IMD 14 may implement one or more timers to ensure that therapy adjustments are associated with the correct posture state intended by patient 12 when the therapy adjustment was made. In some examples, patient 12 may make a therapy adjustment that overrides a therapy parameter value automatically selected by IMD 14 in response to a sensed patient posture state. In other examples, IMD 14 may be in an operating mode in which IMD 14 does not automatically select a therapy parameter value based on a sensed patient posture state, but rather selects the therapy parameter value selected by patient 12 via the therapy adjustment. In either example, a therapy adjustment provided by patient 12 is a manual selection of a therapy parameter value. The therapy parameter value may be perceived by patient 12 as providing effective therapy.

When patient 12 makes a therapy adjustment (e.g., a change to one of the stimulation parameter values that defines the stimulation therapy), the therapy adjustment is intended for a particular posture state. For example, patient 12 may perceive a need to make the adjustment to the therapy parameter value because of the therapeutic efficacy (or lack thereof) of the therapy delivered by IMD 14 while patient 12 is in a particular posture state. Although some therapy adjustments may be made and intended for the posture state currently occupied by patient 12, patient 12 sometimes anticipates the next posture state and makes the therapy adjustment prior to transitioning to the intended posture state. Thus, in some examples, IMD 14 implements a posture search timer having a search period and a posture stability timer having a stability period after any therapy adjustment in order to match the therapy adjustment to the appropriate posture state. The IMD 14 may start the posture search timer upon detecting a therapy adjustment by patient 12, and IMD 14 may start the posture stability timer upon detecting a posture state transition.

When used together, the posture search timer and the posture stability timer allow therapy system 10 to associate a therapy adjustment to a later posture state (e.g., a posture state undertaken by patient 12 after providing the therapy adjustment input). The therapy adjustment is only associated with the final posture state if the final posture state is sensed within a search period defined by the posture search timer and continues for at least a stability period defined by the posture stability timer. That is, the therapy adjustment is associated with a final posture state only when a final posture state is detected within the search period of the posture search timer and is maintained beyond the stability period of the posture stability timer. In this manner, therapy adjustments are not associated with a posture state that does not remain constant (e.g., a transitory posture state) or is not occupied soon enough after the therapy adjustment.

In other examples, IMD 15 does not utilize a posture search timer, and only utilizes the posture stability timer. As a result, in some examples, a therapy adjustment is associated with the final posture state regardless of the duration of time in which the final posture is sensed relative to the therapy adjustment, as long as the posture state is maintained for a stability period defined by the posture stability timer. Examples in which both a search timer and a stability timer are used are primarily referred to herein. However, the systems, devices, and techniques described herein may also be used to associate therapy adjustments with one or more posture states with the aid of a posture stability timer and not a posture search timer.

In accordance with techniques described herein, after receiving a therapy adjustment and associating the therapy adjustment with a patient posture state, e.g., in a memory of IMD 14 or programmer 20, a stability indication may be associated with the patient posture state in the memory. The stability indication may be, for example, a value, flag, or signal. In general, the stability indication indicates that the therapy adjustment received from patient 12 (or another user) has been specifically associated with the patient posture state associated with the stability indication. In this way, the stability indication tracks the posture states for which patient 12 has provided input specifying an adjustment to a therapy parameter value. Posture states with stability indications are in contrast to posture states for which the patient has not provided input. In some examples, after the association with a stability indication, a posture state is never unassociated with the stability indication. Although patient 12 may continue to provide therapy adjustments adjusting one or more therapy parameter values for the posture state, IMD 14 does not remove the stability indication associated with the posture state. In some examples, a clinician may reset the stability indications such that one or more posture states previously associated with stability indications are no longer associated with stability indications.

The patient posture state may be related to other patient posture states, such as posture states for which therapy parameter values are similar, if not identical. For example, the posture state module of IMD 14 may be programmed to detect a lying front posture state in which the patient is lying on a front side (e.g., a ventral side) of the body, a lying back posture state in which the patient is lying on a back side (e.g., a dorsal side) of the body, lying right posture state in which the patient is lying on a right side of the body, and a lying left posture state in which the patient is lying on a left side of the body. In some examples, IMD 14 identifies the lying front, lying back, lying right, and lying side posture states as being related. As another example, IMD 14 may identify an upright posture state and an upright and active posture state as being related.

For the related posture states, patient 12 may not distinguish between the postures and may perceive the postures as affecting the patient condition or therapy delivery in similar manners. In addition, the therapy parameter values that provide efficacious therapy to patient 12 for each of the related posture states may be substantially similar or identical. Posture states may be identified as being related using any suitable technique. For example, a clinician may link related posture states together in a memory of the therapy system (e.g., IMD 14 or programmer 20), or IMD 14 or programmer 20 may automatically determine posture states as being related based on the similarity of the therapy parameter values associated with the posture states.

In other examples, posture states may be considered related based on the posture state definitions with which IMD 14 detects the posture states. As an example, if the posture states are defined by three-dimensional posture spaces, such as posture cones, the posture states associated with posture spaces having similar absolute orientations relative to a known vector (e.g., a vertical vector) may be linked as being related. As another example, lying back, lying front, lying right, and lying may have similar cosines relative to an upright vector, and, therefore, may be grouped together as related postures.

Figure 8A:
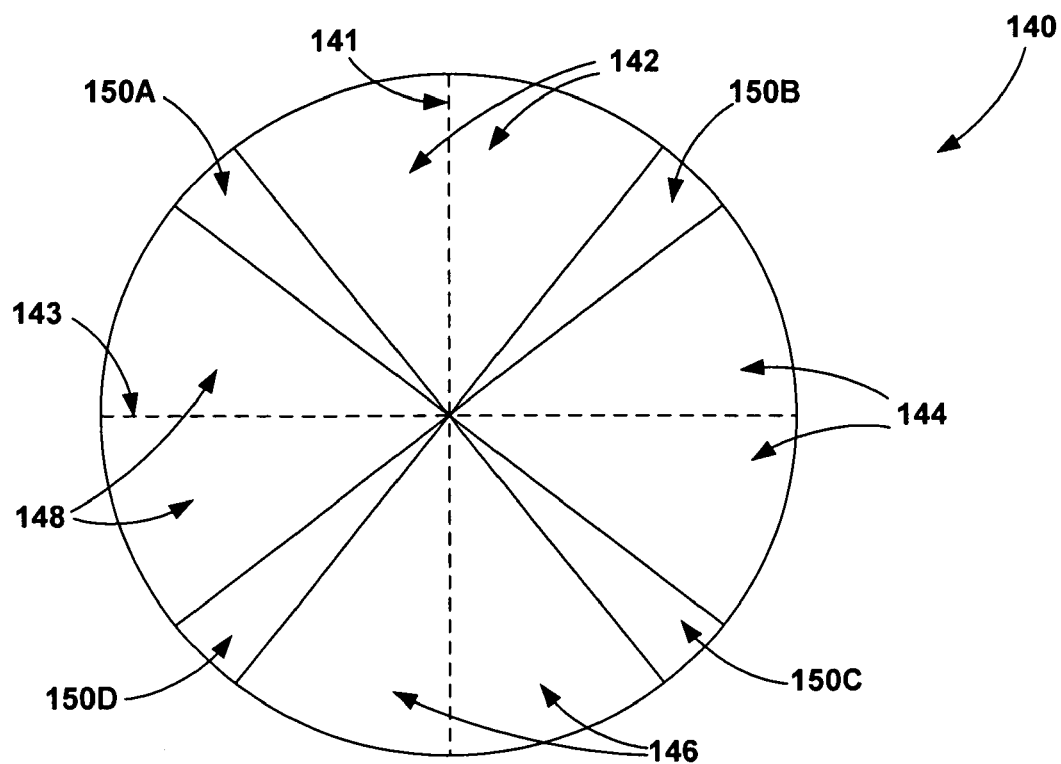
FIGS. 8A-8C are conceptual illustrations of example posture state spaces within which postures state reference data may define the posture state of a patient.
Figure 8B:
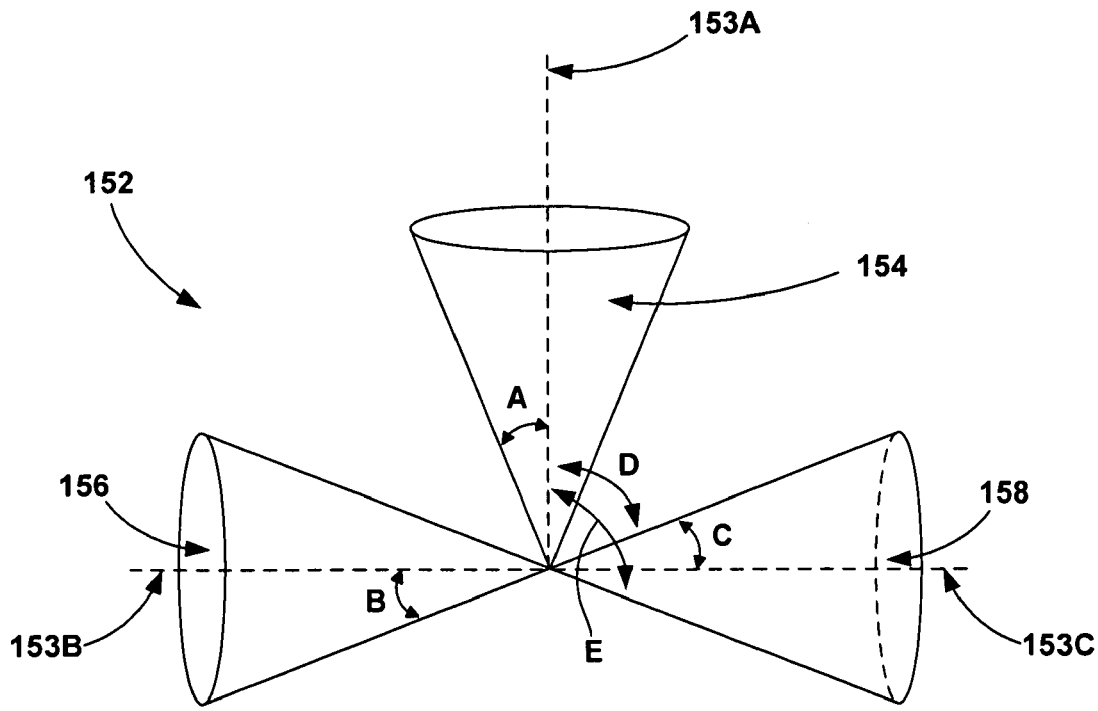
Figure 8C:
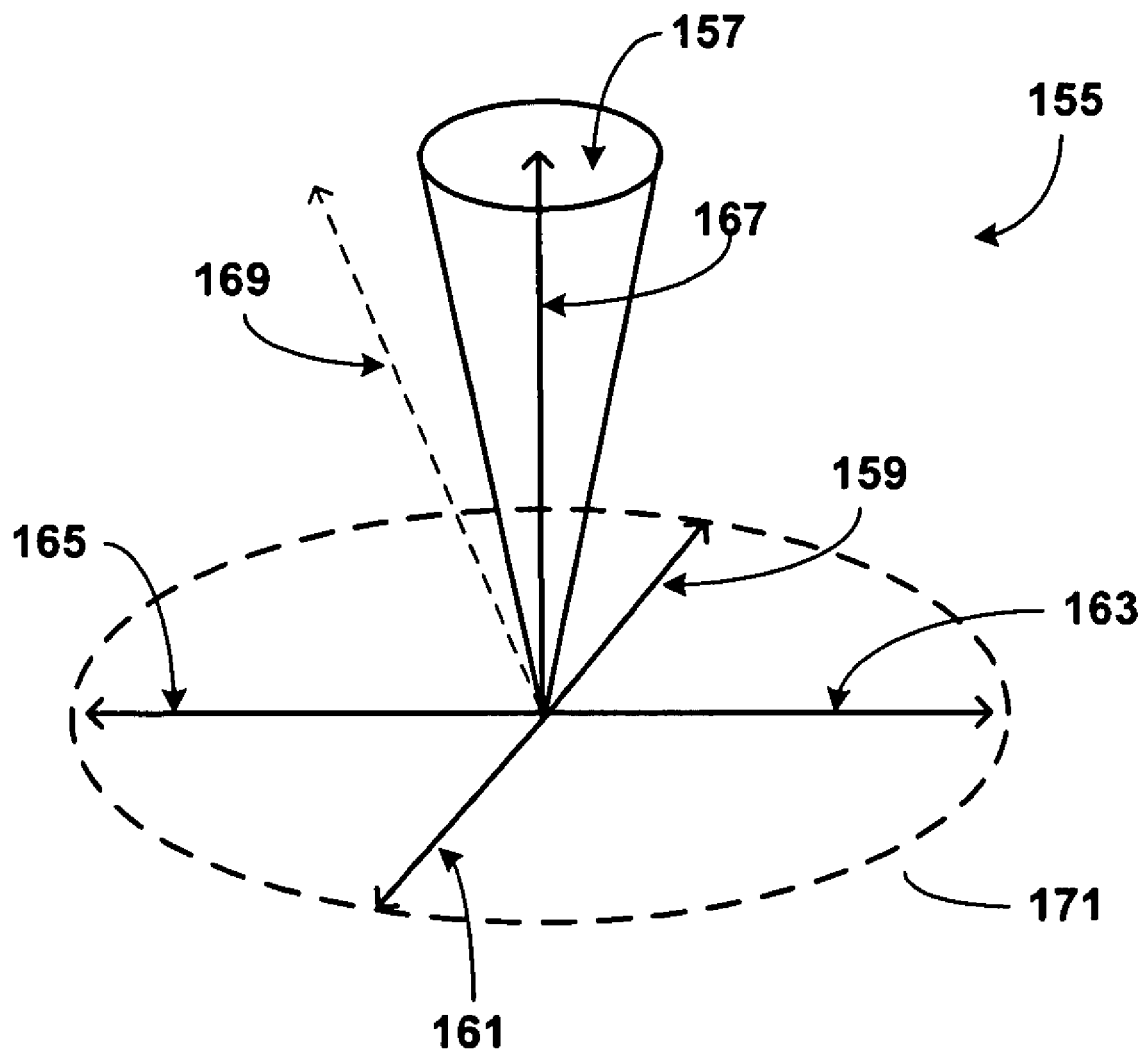

As described with respect to FIGS. 8A-8C, in some examples, a posture cone may be defined by a reference coordinate vector for a given posture state in combination with a distance or angle defining a range of coordinate vectors within a cone surrounding the posture reference coordinate vector. Thus, in some examples, posture states having similar angles or distances relative to a reference coordinate vector may be grouped together as related postures. For example, lying back, lying front, lying right, and lying posture cones may have similar absolute angles or absolute distances relative to an upright vector, and, therefore, may be grouped together as related postures.

In other examples, a posture cone may be defined by a reference coordinate vector and a range of cosine values computed using the reference coordinate vector as an adjacent vector and any of the outermost vectors of the cone as a hypotenuse vector. If a posture state vector sensed by a posture state sensor of system 10 and the reference coordinate vector produce a cosine value in a specified cosine range, then posture state vector is determined to reside within the posture cone defined by the reference coordinate vector. Thus, some examples, posture states having similar cosine values computed using the same reference coordinate vector may be grouped together as related postures.

In addition to associating a therapy adjustment with a posture state, therapy system 10 updates therapy parameter values for related patient posture states that are not associated with respective stability indications based on the therapy adjustment. The absence of a stability indication indicates that patient 12 has not inputted a therapy adjustment specific to the respective related posture state. As a result, for the related posture states that are not associated with stability indications, the associated therapy parameter values may float until patient 12 adjusts the therapy parameter value associated with the respective related posture state. A therapy parameter value floats in the sense that the therapy parameter value varies based on therapy adjustments provided by patient 12 for at least one related posture state. In this way, the therapy parameter values for posture states not associated with stability indications may float to another value when patient 12 provides a therapy adjustment for a related posture state.

Examples of updates to therapy parameter values that may be made include, for example, applying the therapy adjustment to the therapy parameter values of the related patient posture states not associated with a stability indication. For example, the therapy parameter values associated with related patient posture states may be updated to be identically or substantially equal to the therapy parameter value associated with the sensed patient posture state. In other words, while the other related patient posture states remain undefined by a specific user adjustment, they inherit the therapy parameter value of a stable patient posture state or a therapy parameter value that is based on a plurality of stable posture states. As another example, the net change in the therapy parameter value resulting from the therapy adjustment may be applied to the therapy parameter values associated with related patient posture states. In some examples, the therapy parameter values may be updated to maintain a predetermined ratiometric balance between the therapy parameter values of the different patient posture states. In other examples, if more than one related posture state is associated with a stability indication, the therapy parameter values associated with related patient posture states not associated with stability indications may be set at the lowest, highest, or average value of the therapy parameter values associated with posture states associated with a stability indication.

Therapy system 10 dynamically adapts therapy parameter values with which IMD 14 delivers posture responsive therapy by automatically adjusting a therapy parameter value associated with a posture state that is not associated with a stability indication based on a therapy adjustment provided by patient 12 for a related patient posture state. A therapy adjustment specific to a sensed patient posture state is useful for predicting and anticipating a therapy parameter value that provides efficacious therapy to patient 12 in related patient posture states. Because therapy delivery may have similar effects on patient 12 for each of a plurality of related posture states, a user adjustment for one patient posture may indicate or suggest that a similar adjustment will provide efficacious therapy to patient 12.

After each posture state in a group of related posture states is associated with a stability indication, IMD 14 (or programmer 20) may stop the automatic association of one therapy adjustment to related posture states. While patient 12 may continue making therapy adjustments for a specific posture state, IMD 14 only updates the sensed posture state with the therapy adjustment.

External programmer 20 may present posture state data stored in IMD 14 from the detected posture states of patient 12. The posture state data may be acquired by external programmer 20 to generate posture state information, e.g., therapy adjustment information. IMD 14 may also store any associations between the therapy adjustments and the posture states for which the therapy adjustments were intended during a record mode, i.e., therapy adjustment information. By recording all therapy adjustments made for a program in each of the posture states, external programmer 20 may be able to present therapy adjustment information to the user that indicates patient 12 desired specific stimulation parameters. For example, as described in U.S. Patent Application Publication No. 2010/0010588 by Skelton et al., entitled "ASSOCIATING THERAPY ADJUSTMENTS TO PATIENT POSTURE STATES" and filed on Apr. 30, 2009, the user may be able to identify the most recent stimulation parameters desired by patient 12, the minimum and maximum allowable amplitudes, or even the quantified number of therapy adjustments to indicate that patient 12 is either satisfied with a program or cannot find suitable parameters for a program with many therapy adjustments. U.S. Patent Application Publishing No. 2010/0010588 by Skelton et al. is incorporated herein by reference in its entirety.

The therapy adjustment information stored during the record mode may be presented in any number of different manners. For example, the user interface may present each program of a group and the respective number of therapy adjustments and the range of such amplitudes defined by the therapy adjustments. Alternatively, the user interface may also, or instead, present the last (i.e., most recent, amplitude used by patient 12 to deliver therapy with each program). In any manner, the therapy adjustment information may be presented in a graphical, numerical, or textual mode on external programmer 20. The user may be able to customize the presentation of the therapy adjustment information in some examples.

In some examples, external programmer 20 may utilize the associations of the therapy adjustments to posture states in order to further minimize time needed to program all therapy programs. When presenting the amplitude ranges of the therapy adjustments for each therapy program, the user may be able to provide a single confirmation input that sets the amplitude for all programs to some nominal therapy parameter, for example. The nominal therapy parameter may be a minimum amplitude associated with the program and posture state, the last amplitude associated with the program and posture state, or some other therapy parameter already stored by IMD 14 in association with each therapy program and posture state. The therapy parameter is nominal in the sense that it refers to a parameter value by a name that is descriptive of the value, rather than to a specific, absolute parameter value. In cases where a program has not been associated with any therapy adjustment, no new stimulation parameter may be programmed to the program.

IMD 14 may be constructed with a biocompatible housing, such as titanium or stainless steel, or a polymeric material such as silicone or polyurethane, and surgically implanted at a site in patient 18 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other suitable location to secure IMD 14. Leads 16 may be tunneled from IMD 14 through tissue to reach the target tissue adjacent to spinal cord 18 for stimulation delivery.

Figure 1B:
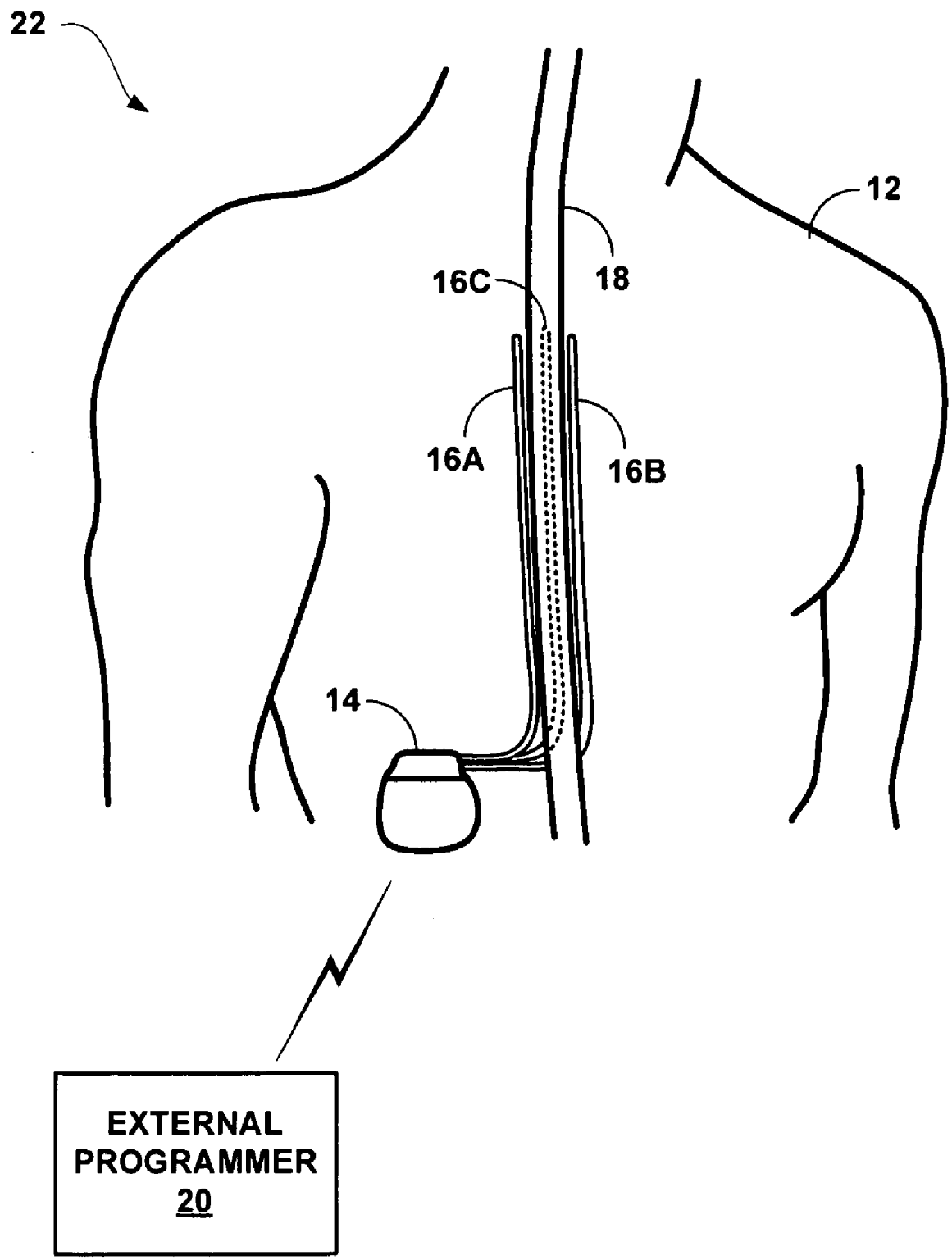
FIG. 1B is a conceptual diagram illustrating another example implantable therapy system including three implantable stimulation leads.

FIG. 1B is a conceptual diagram illustrating stimulation system 22 including three implantable stimulation leads 16A, 16B, 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. The number and configuration of leads 16 may be stored within external programmer 20 in order to programmer 20 appropriately program stimulation therapy or assist in the programming of stimulation therapy.

In some examples, leads 16A and 16B include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible, whereby the number in the configuration indication refers to the number of electrodes in a particular electrode column, which may be defined by a lead 16A-16C. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
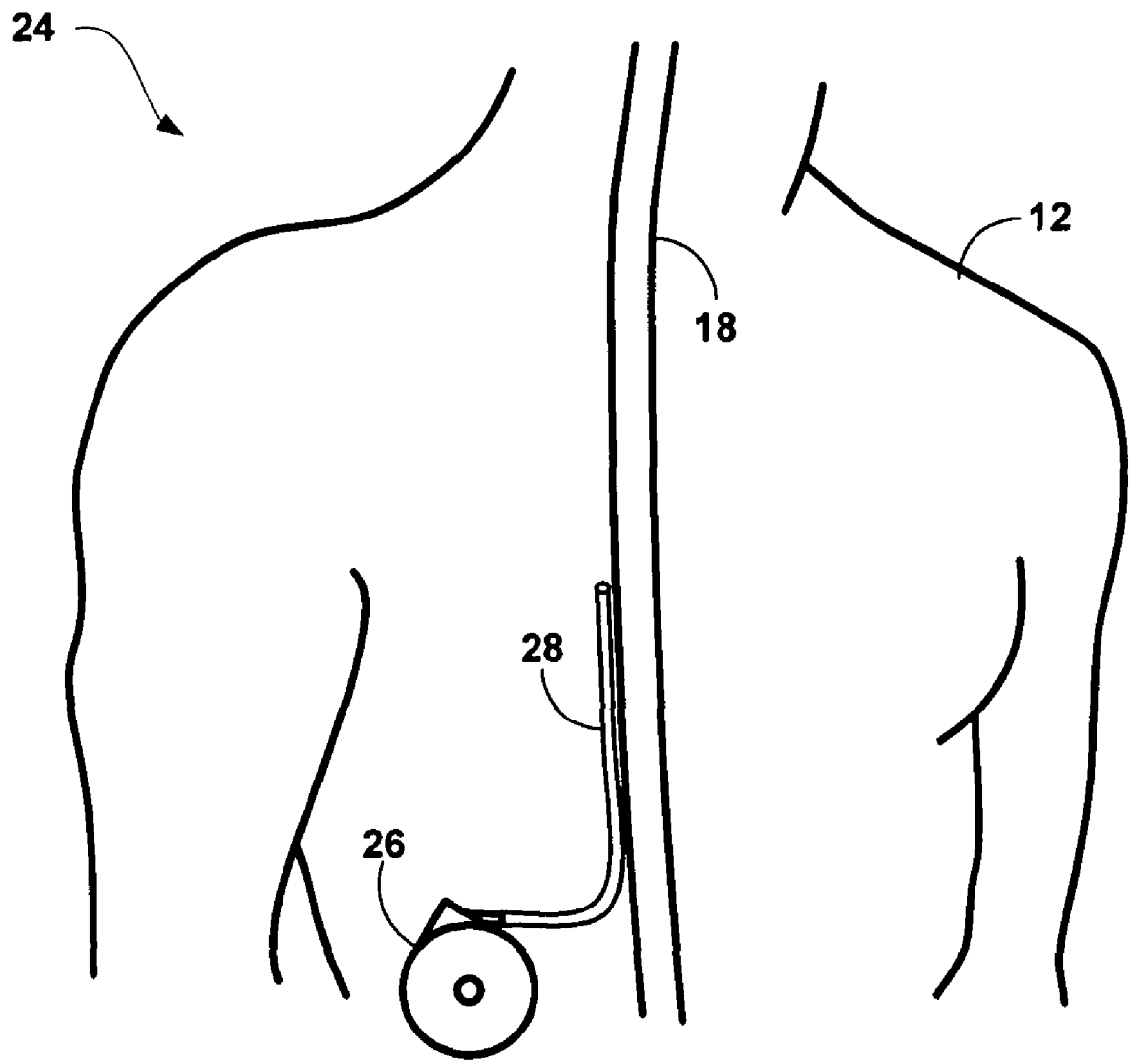
FIG. 1C is a conceptual diagram illustrating an implantable drug delivery system including a drug delivery device and a delivery catheter.

FIG. 1C is a conceptual diagram illustrating an implantable drug delivery system 24 including one delivery catheter 28 coupled to IMD 26. As shown in the example of FIG 1C, drug delivery system 24 is substantially similar to systems 10 and 22. However, drug delivery system 24 performs the similar therapy functions via delivery of the delivery of therapeutic agents instead of electrical stimulation. IMD 26 functions as a drug pump in the example of FIG 1C, and IMD 26 communicates with external programmer 20 to initialize therapy or modify therapy during operation. In addition, IMD 26 may be refillable to allow chronic drug delivery.

A fluid delivery port of catheter 28 may be positioned within an intrathecal space or epidural space of spinal cord 18, or, in some examples, adjacent nerves that branch off of spinal cord 18. Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some examples, IMD 26 may be an external device that includes a percutaneous catheter that delivers a therapeutic agent to patient 12, e.g., in the same manner as catheter 28. Alternatively, the percutaneous catheter may be coupled to catheter 28, e.g., via a fluid coupler. In other examples, IMD 26 may include both electrical stimulation capabilities, e.g., as described with respect to IMD 14 (FIG. 1A), and drug delivery therapy.

IMD 26 may also operate using parameters that define the method of drug delivery. IMD 26 may include programs, or groups of programs, that define different delivery methods for patient 12. For example, a program that controls delivery of a drug or other therapeutic agent may include a titration rate or information controlling the timing of bolus deliveries. Patient 12 may use external programmer 20 to adjust the programs or groups of programs to regulate the therapy delivery.

Just as with IMD 14 (FIG. 1A), IMD 26 includes a posture state module that monitors the patient 12 posture state and adjusts therapy accordingly. For example, the posture state module may indicate that patient 12 transitions from lying down to standing up. In some examples, IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

The techniques described herein for programming IMD 14 (FIG. 1A), which provides electrical stimulation therapy may also be implemented to program IMD 26. For example, during the course of therapy delivery by IMD 26, patient 12 may make an adjustment to a therapy parameter value with which IMD 25 delivers a therapeutic agent to patient 12. In accordance with techniques described herein, therapy system 24 (e.g., IMD 26 or programmer 20) associates the adjusted therapy parameter value with a sensed patient posture state, which is determined with the aid of the posture state module, a posture search timer and a posture stability timer that track therapy adjustments and posture state changes in real time. After receiving a therapy adjustment and associating the therapy adjustment with a sensed posture state, therapy system 24 may associate a stability indication with the sensed posture state. Therapy parameter values associated with related patient posture states that are not associated with a stability indication are also updated based on the therapy adjustment.

While IMD 14 is primarily referred to throughout the disclosure, the systems, devices, and techniques for programming IMD 14 are also applicable to IMD 26. Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

Figure 2:
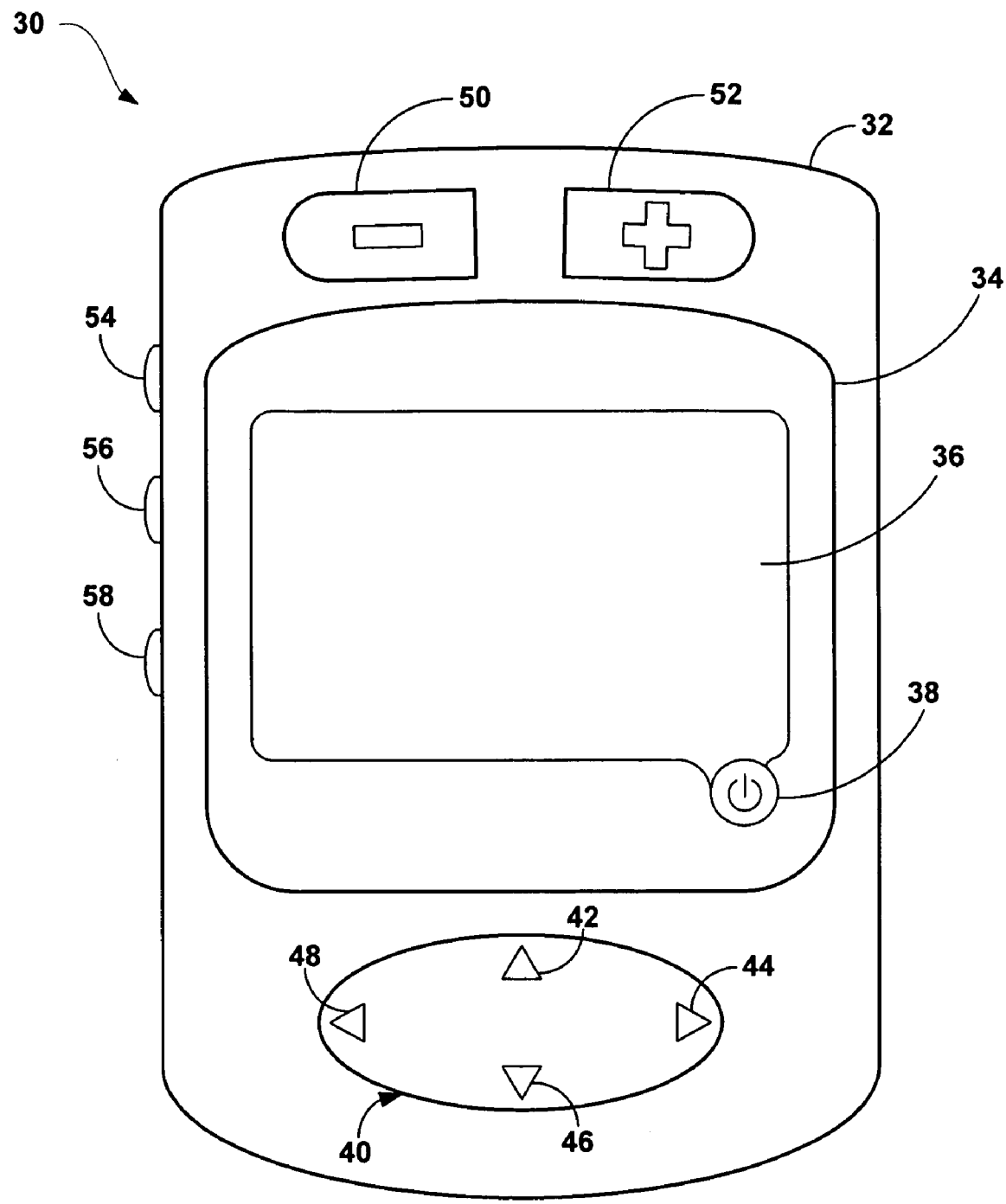
FIG. 2 is a conceptual diagram illustrating an example patient programmer for programming therapy delivered by an implantable medical device.

FIG. 2 is a conceptual diagram illustrating an example patient programmer 30 for programming stimulation therapy delivered by an IMD. Patient programmer 30 is an example of external programmer 20 illustrated in FIGS. 1A, 1B and 1C and may be used to program either IMD 14 or IMD 26. In other examples, patient programmer 30 may be used with an external medical device. As shown in FIG. 2, patient programmer 30 provides a user interface (not shown) for a user, such as patient 12, to manage and program stimulation therapy. Patient programmer 30 is protected by housing 32, which substantially encloses circuitry necessary for patient programmer 30 to operate.

Patient programmer 30 also includes display 36, power button 38, decrease button 50, increase button 52, stimulation ON button 54, stimulation OFF button 56, and sync button 58. Cover 34 protects display 36 from being damaged during user manipulation (e.g., interaction) with patient programmer 30. Patient programmer 30 also includes control pad 40 which allows a user to navigate through items displayed on display 36 in the direction of arrows 42, 44, 46, and 48. In some examples, the buttons and control pad 40 take the form of soft keys (e.g., with functions and contexts indicated on display 36), with functionality that may change, for example, based on current programming operation or user preference. In alternative examples, display 36 is a touch screen with which patient 12 may directly interact without the use of control pad 40. A touch screen display may eliminate the use of buttons, such as increase button 52 and decrease button 50, although buttons may be used in addition to a touch screen display.

In the illustrated example, patient programmer 30 is a hand held device. Patient programmer 30 may accompany patient 12 throughout a daily routine. In some cases, patient programmer 30 may be used by a clinician when patient 12 visits the clinician in a hospital or clinic. In other examples, programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 30 ON or OFF as desired by patient 12. Patient 12 may control the illumination level, or backlight level, of display 36 by using control pad 40 to navigate through the user interface and increase or decrease the illumination level with decrease and increase buttons 50 and 52.

In some examples, illumination may be controlled by a knob that rotates clockwise and counter-clockwise to control patient programmer 30 operational status and display 36 illumination. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may include any one or more of liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMDs 14 or 26. For example, patient programmer 30 may provide a scrollable list of groups, and a scrollable list of programs within each group, via display 36. In addition, display may present a visible posture state indication.

In some examples, programmer 30 presents a visible posture state indication to a user (e.g., patient 12) via display 36. In addition, display 36 may present therapy adjustment information stored during the record mode of IMD 14, and, in some examples, the related posture states that were updated based on the therapy adjustment. As described herein, patient programmer 30 may be configured to perform any tasks described with respect to clinician programmer 60 or another external programmer 20.

Patient 12 or another user may interact with control pad 40 to navigate through items displayed on display 36. Patient 12 may press control pad 40 on any of arrows 42, 44, 46, and 48 in order to move between items presented on display 36 or move to another screen not currently shown on display 36. In some examples, pressing the middle of control pad 40 selects one or more highlighted items presented on display 36. In other examples, scroll bars, a scroll wheel, individual buttons, or a joystick may perform the complete or partial functions of control pad 40. In addition, in some examples, control pad 40 includes a touch pad that allows patient 12 to move a cursor within the user interface displayed on display 36 to manage therapy or review posture state information.

Decrease button 50 and increase button 52 provide an input mechanism for patient 12, e.g., that facilitates therapy parameter adjustments. In general, activation of decrease button 50 may decrease the value of a highlighted stimulation parameter presented on display 36. In contrast, activation of increase button 52 may increase the value of a highlighted stimulation parameter. Buttons 50, 52 may be activated by depressing the respective button. In some cases, patient 12 incrementally increases or decreases a therapy parameter value by activating the respective button 50, 52 for each incremental change. While buttons 50 and 52 may be used to control the value of any stimulation parameter, buttons 50 and 52 may also control patient feedback input. When either button 50 and 52 is selected, patient programmer 30 may initialize communication with IMD 14 or 26 to change therapy accordingly.

When depressed by patient 12, stimulation ON button 54 directs programmer 30 to generate a command that is transmitted to IMD 14, where the command instructs IMD 14 to turn on stimulation therapy. Stimulation OFF button 56 turns off stimulation therapy when depressed by patient 12. Sync button 58 causes patient programmer 30 to communicate with IMD 14 within a substantially minimal amount of time from activation of sync button 58. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example shown in FIG. 2, patient 12 may use control pad 40 to adjust the volume, contrast, illumination, time, and measurement units of patient programmer 30.

In some examples, buttons 54 and 56 may be configured to perform operational functions related to stimulation therapy or the use of patient programmer 30. For example, buttons 54 and 56 may control the volume of audible sounds produced by programmer 30, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display brightness and contrast, or other similar options. In alternative examples, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative examples of patient programmer 30 may include other input mechanisms such as a keypad, microphone, camera lens, or any other media input that allows the user to interact with the user interface provided by patient programmer 30.

In alternative examples, the buttons of patient programmer 30 may perform different functions than the functions provided in FIG. 2 and/or may have a different arrangement. In addition, other examples of patient programmer 30 may include different button layouts or different numbers of buttons. For example, patient programmer 30 may even include a single touch screen that incorporates all user interface functionality with a limited set of buttons or no other buttons.

Figure 3:
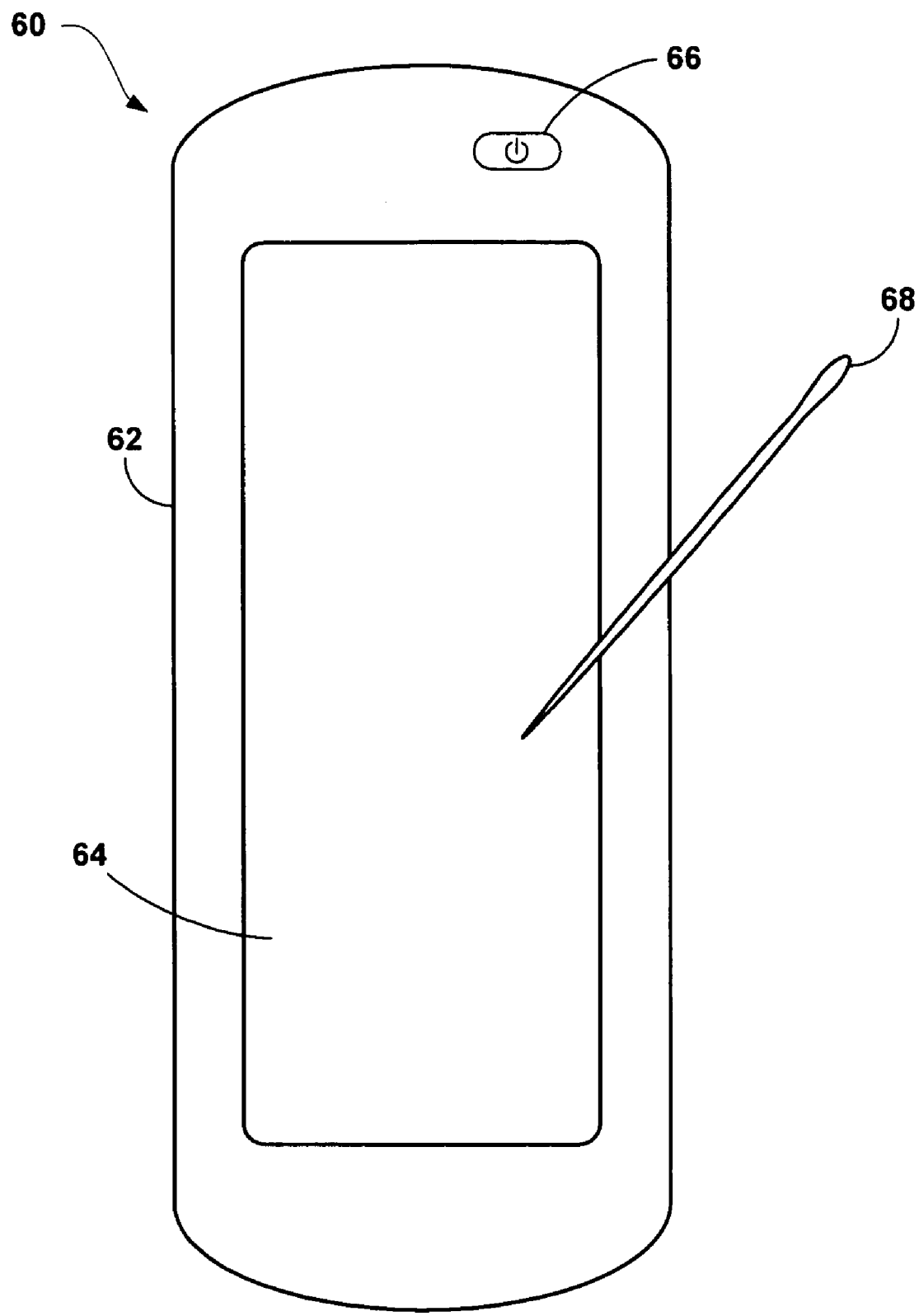
FIG. 3 is a conceptual diagram illustrating an example clinician programmer for programming therapy delivered by an implantable medical device.

FIG. 3 is a conceptual diagram illustrating an example clinician programmer 60 that may be used to program therapy delivered by an IMD, such as IMD 14 (FIG. 1A) or IMD 26 (FIG. 1C). Clinician programmer 60 is an example of external programmer 20 illustrated in FIGS. 1A, 1B and 1C and may be used with either IMD 14 or IMD 26. In alternative examples, clinician programmer 60 may be used with an external medical device. As shown in FIG. 3, clinician programmer 60 provides a user interface (not shown) for a user, such as a clinician, physician, technician, or nurse, to manage and program stimulation therapy. Clinician programmer 60 is protected by housing 62, which encloses circuitry necessary for clinician programmer 60 to operate.

Clinician programmer 60 is used by the clinician or other user to modify and review therapy to patient 12. The clinician may define each therapy parameter value for each of the programs that define stimulation therapy. The therapy parameters, such as amplitude, may be defined specifically for each of the posture states that patient 12 will be engaged in during therapy. The initial therapy parameter selections made by the clinician with the aid of clinician programmer 60 may be later modified by patient 12, as described with respect to FIGS. 17 and 18. The clinician may also use clinician programmer 60 to define each posture state of patient 12, e.g., by defining posture state spaces described with respect to FIGS. 8A-8C or some other technique for associating posture state sensor output to the posture state of patient 12.

Clinician programmer 60 includes display 64 and power button 66. In the example shown in FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some examples, the user may be able to touch display 64 with a finger, pen, or any other pointing device. In alternative examples, clinician programmer 60 may include one or more buttons, keypads, control pads, touch pads, or other devices that accept user input, similar to patient programmer 30.

In the illustrated example, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some examples, clinician programmer 60 may be a larger device that may be less portable, such as a notebook computer, workstation, or even a remote computer that communicates with IMD 14 or 26 via a remote telemetry device.

Most, if not all, of clinician programmer 60 functions may be completed via the touch screen of display 64. The user may program stimulation parameter values, modify therapy programs or groups, retrieve stored therapy data from an IMD or another device, retrieve posture state information from an IMD or another device, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

Clinician programmer 60 may also allow the clinician to view historical therapy adjustment information stored in IMD 14 during therapy. As previously discussed, the therapy adjustment information includes any associations created between therapy parameter value adjustments and posture states for each program that delivers automatic posture responsive stimulation. The clinician may initially orient IMD 14 to patient 12 and enable the record mode for IMD 14 to store any associations as therapy adjustment information. Clinician programmer 60 may then acquire the therapy adjustment information from IMD 14 and present the information to the clinician in order to allow continued effective therapy modifications.

In some examples, clinician programmer 60 may also allow the clinician to adjust the search period of the posture search timer and the stability period of the posture stability timer. The posture search timer and the posture stability timer enable IMD 14 to determine the posture state with which a therapy adjustment should be associated. Depending upon the condition of patient 12 or the clinician preferences, the clinician may desire to adjust the search period and stability period to most accurately reflect the intentions of patient 12. For example, if patient 12 has a habit of adjusting therapy long before making a change to the posture state or patient 12 takes a long time to assume a desired posture state, the clinician may desire to increase the search period and stability period. In some examples, clinician programmer 60 may suggest appropriate search periods and stability periods for patients diagnosed with particular conditions that may hinder their movement or involve multiple oscillations in posture state before settling on the final posture state.

In addition, clinician programmer 60 may present suggested therapy parameters to the clinician based upon the stored therapy adjustment information in IMD 14. In one example, clinician programmer 60 may simply present an amplitude range determined by the therapy adjustments for each program and posture state. The clinician may then set the amplitude of each program to a nominal therapy parameter presented on display 64 of clinician programmer 60. For example, the nominal therapy parameter may be the minimum amplitude used by patient 12 for each program. Alternatively, clinician programmer 60 may present the last therapy adjustment for each program and posture state, or an average therapy adjustment. Clinician programmer 60 may then set the therapy parameter for all displayed programs with a single confirmation input from the clinician. This single input may decrease clinician programming time.

Further, clinician programmer 60 may present a suggested therapy parameter to the clinician for each program and posture state that is based upon the therapy adjustment information. The suggested therapy parameter may or may not be a parameter that was used from a therapy adjustment. Clinician programmer 60 may utilize a guided algorithm that attempts to generate a suggested therapy parameter that the clinician desires to free the clinician from manually determining the best therapy parameter for each program. Clinician programmer 60 may utilize one algorithm or receive a guided algorithm input from the clinician that customizes how clinician programmer 60 generates the suggested therapy parameters. For example, clinician programmer 60 may use a target trend guided algorithm that weights more recent therapy adjustments so that the suggested therapy parameters are more representative is recent patient 12 response to stimulation therapy.

In some cases, all processing may be performed in IMD 14 and information may be transmitted to clinician programmer 60 for presentation to the clinician. Alternatively, IMD 14, clinician programmer 60, patient programmer 30, or another computing device may share in the processing duties of therapy adjustment information and any other data prior to presenting the information on clinician programmer 60.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
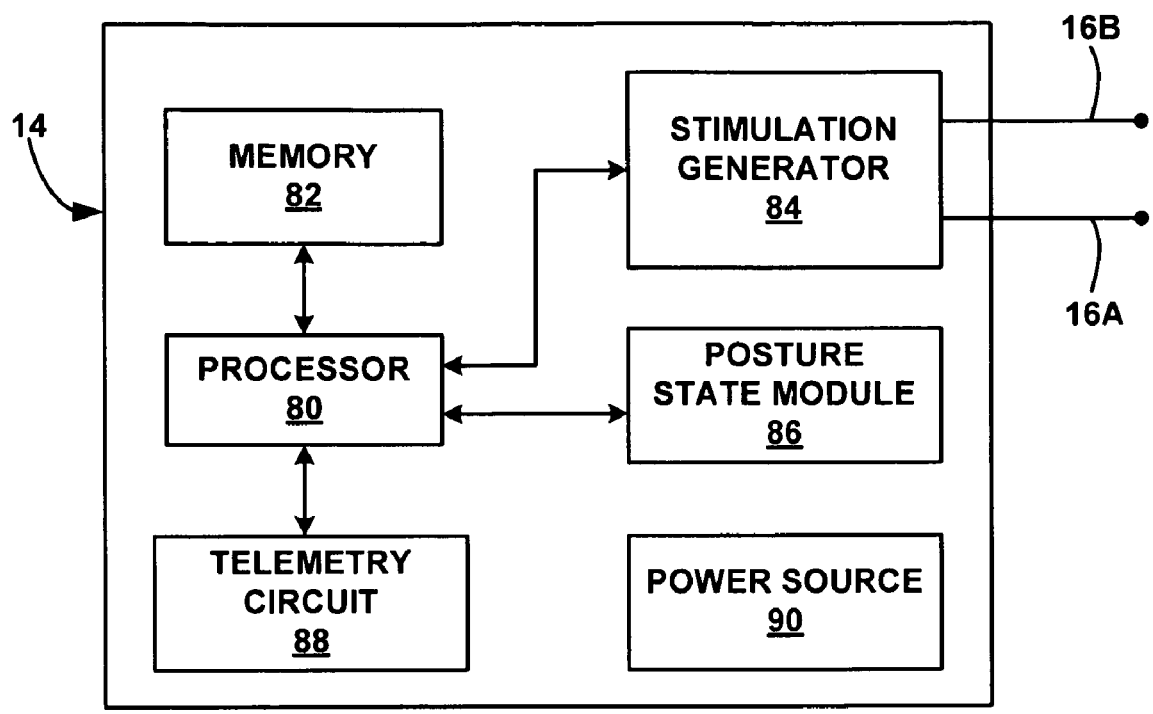
FIG. 4 is a functional block diagram illustrating various components of an implantable electrical stimulator.

FIG. 4 is a functional block diagram illustrating various components of an example IMD 14. In the example shown in FIG. 4, IMD 14 includes a processor 80, memory 82, stimulation generator 84, posture state module 86, telemetry circuit 88, and power source 90. Stimulation generator 84 forms a therapy delivery module.

Memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 82 may store instructions for execution by processor 80, stimulation therapy information, posture state information (e.g., posture state definitions, information associating posture states with therapy programs, and the like), posture state indications, and any other information regarding therapy or patient 12. Therapy information may be recorded for long-term storage and retrieval by a user, and the therapy information may include any data created by or stored in IMD 14. Memory 82 may include separate memories for storing instructions, posture state information, program histories, and any other data that may benefit from separate physical memory modules.

Processor 80 controls stimulation generator 84 to deliver electrical stimulation via electrode combinations defined by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to processors described herein may be provided by a hardware device and embodied as software, firmware, hardware, or any combination thereof.

Stimulation generator 84 may include stimulation generation circuitry to generate stimulation pulses or continuous waveforms, and, in some examples, switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations when the therapy must be delivered to a different location within patient 12. In other examples, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode configuration, e.g., electrode combination and associated electrode polarities, may be represented by a data stored in a memory location, e.g., in memory 82, of IMD 14. Processor 80 may access the memory location to determine the electrode combination and control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy. In other examples, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

According to examples described herein, such stimulation parameters may be adjusted to modify stimulation therapy delivered by IMD 14 based on the detected posture state of patient 12. In some examples, processor 80 may detect a posture state of patient 12 via posture state module 86 that indicates that a modification of the stimulation therapy is appropriate, e.g., according to instructions stored in memory 82. Processor 80 may access instructions for modifying the stimulation therapy based on the patient 12 posture state, e.g., by changing from a stimulation program appropriate for the previous posture state to a stimulation program appropriate for patient's current posture state.

An example range of electrical stimulation parameters likely to be effective in treating chronic pain, e.g., when applied to spinal cord 18 (FIG. 1A), are listed below. While stimulation pulses are described, stimulation signals may be of any of a variety of forms such as stimulation pulses, continuous time signals (e.g., sine waves) or the like.

1. Pulse Rate: between approximately 0.5 Hz and approximately 1200 Hz, such as between approximately 5 Hz and approximately 250 Hz, or between approximately 30 Hz and approximately 130 Hz.

2. Amplitude: between approximately 0.1 volts and approximately 50 volts, such as between approximately 0.5 volts and approximately 20 volts, or between approximately 1 volt and approximately 10 volts. In other examples, a current amplitude may be defined as the biological load in the voltage that is delivered. For example, the range of current amplitude may be between approximately 0.1 milliamps (mA) and approximately 50 mA.

3. Pulse Width: between approximately 10 microseconds and approximately 5000 microseconds, such as between approximately 100 microseconds and approximately 1000 microseconds, or between approximately 180 microseconds and approximately 450 microseconds.

In other applications, different ranges of parameter values may be used. For DBS, as one example, alleviation or reduction of symptoms associated with Parkinson's disease, essential tremor, epilepsy, psychiatric disorders or other disorders may make use of stimulation having a pulse rate in the range of approximately 0.5 Hz to approximately 1200 Hz, such as approximately 5 Hz to approximately 250 Hz, or approximately 30 Hz to approximately 185 Hz, and a pulse width in the range of approximately 10 microseconds and 5000 microseconds, such as between approximately 60 microseconds and approximately 1000 microseconds, between approximately 60 microseconds and approximately 450 microseconds, or between approximately 60 microseconds and approximately 150 microseconds. Amplitude ranges such as those described above with reference to SCS, or other amplitude ranges, may be used for different DBS applications.

Processor 80 accesses stimulation parameters in memory 82, e.g., as therapy programs and groups of programs. Upon selection of a particular program group, processor 80 may control stimulation generator 84 to generate and deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

Posture state module 86 allows IMD 14 to sense the patient posture state, e.g., posture, activity or any other static position or motion of patient 12. In the example shown in FIG. 4, posture state module 86 includes one or more accelerometers, such as three-axis accelerometers, capable of detecting static orientation or vectors in three-dimensions. Example accelerometers include a micro-electromechanical accelerometer. In other examples, posture state module 86 may alternatively or additionally include one or more gyroscopes, pressure transducers, piezoelectric crystals, or other sensors to sense the posture state of patient 12. Posture state information generated by posture state module 86 and processor 80 may correspond to an activity and/or posture undertaken by patient 12 or a gross level of physical activity, e.g., activity counts based on footfalls or the like.

Posture state information from posture state module 86 may be stored in memory 82 for later review by a clinician, used to adjust therapy, present a posture state indication to patient 12 via patient programmer 30, or some combination thereof. As an example, processor 80 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture. IMD 14 may also store which group or program was being used to deliver therapy when patient 12 was in the sensed posture. Further, processor 80 may also adjust therapy for a new posture when posture state module 86 indicates that patient 12 has in fact changed postures. Therefore, IMD 14 may be configured to provide posture responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

As described herein, the posture state data, or raw data of the posture state information, is stored to be later used. The posture state information may also be used in addition to the therapy adjustment information when the user desires to view more detailed information related to the posture states engaged by patient 12. Memory 82 may store all of the posture state data and therapy adjustment data detected during therapy or use of IMD 14, or memory 82 may periodically offload the posture state data and therapy adjustment data to clinician programmer 60 or a different external programmer 20 or device. In other examples, memory 82 may reserve a portion of the memory to store recent posture state data easily accessible to processor 80 for analysis. In addition, older posture state data may be compressed to require less memory until later needed by external programmer 20 or processor 80.

A posture state parameter value from posture state module 86 that indicates the posture state may constantly vary throughout the day of patient 12. A certain activity (e.g., walking, running, or biking) or a posture (e.g., standing, sitting, or lying down) may include multiple posture state parameter values from posture state module 86. Memory 82 stores definitions for each posture state of patient 12. In one example, the definitions of each posture state may be illustrated as a three-dimensional space, e.g., as described with respect to FIGS. 8A-8C. Examples of three-dimensional spaces include, but are not limited to, a posture cone or a toroid (or donut). Whenever the posture state parameter value, e.g., a vector from the three-axis accelerometer of posture state module 86, is within an applicable angle or distance of a reference coordinate vector, or if the sensed posture state vector and the reference coordinate vector produce a cosine value in a specified cosine range, then the posture state vector is determined to reside within the posture cone defined by the reference coordinate vector and processor 80 indicates that patient 12 is in the posture state associated with the cone. In other examples, posture state parameter value from the 3-axis accelerometer may be compared to a look-up table or equation to determine the posture state in which patient 12 currently resides.

Posture responsive stimulation allows IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters can be tedious, requiring patient 12 to, for example, depress one or more keys of patient programmer 30 multiple times during the patient posture state to maintain adequate symptom control. However, as described herein, in some cases, patient 12 manually adjusts one or more therapy parameter values, such as amplitude, pulse width, or pulse rate, associated with a posture state during posture response therapy delivery by IMD 14. Patient 12 may, for example, fine tune the therapy parameter values to provide efficacious therapy after the initial programming of the therapy parameter values by the clinician. IMD 14 stores the therapy adjustments and associates the therapy adjustments with a specific posture state in memory 82. In some examples, the number of therapy adjustments made by patient 12 may eventually decrease over time as the therapy parameter values personalized by patient 12 are stored in IMD 14. In this way, over time, IMD 14 may provide posture state responsive therapy without the need for patient 12 to continue making changes for different postures via patient programmer 30.

Although posture state module 86 is described as including a 3-axis accelerometer, in other examples, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient posture state may be determined from multiple activity sensors placed at various locations on or within the body of patient 12.

In other examples, posture state module 86 may additionally or alternatively be configured to sense one or more additional physiological parameters of patient 12. For example, physiological parameters may include heart rate, muscle activity (e.g., as indicated by electromyography), brain signals (e.g., as indicated by electroencephalogram or electrocorticogram), electrocardiogram, blood pressure, temperature, respiration rate, or pH. These physiological parameters may be used by processor 80, in some examples, to confirm or reject changes in sensed posture state that may result from vibration, patient travel (e.g., in an aircraft, car or train), or some other false positive of posture state.

In some examples, processor 80 processes the analog output of the posture state sensor of posture state module 86 to determine activity and/or posture data. For example, where the posture state sensor comprises an accelerometer, processor 80 or a processor specific to posture state module 86 may process the raw signals provided by the posture state sensor to determine activity counts. In some examples, processor 80 may process the signals provided by the posture state sensor to determine velocity of motion information along each axis. In one example, each of the x-axis, y-axis, and z-axis signals provided by the posture state sensor has both a DC component and an AC component. The DC components describes the gravitational force exerted upon the sensor and can thereby be used to determine orientation of the sensor within the gravitational field of the earth. Assuming the orientation of the sensor is relatively fixed with respect to the patient, the DC components of the x-axis, y-axis, and z-axis signals may be utilized to determine the orientation of patient 12 within the gravitational field, and hence to determine the posture of the patient.

The AC component of the x-axis, y-axis, and z-axis signals yields information about patient motion. In particular, the AC component of a signal may be used to derive a value for an activity describing the patient's motion. This activity may involve a level, direction of motion, or acceleration of the patient.

One technique for determining patient activity is by determining an activity count. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count". The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the motion of patient 12.

As another example, the activity parameter value may be defined describing direction of motion. This activity parameter value may be associated with a vector and an associated tolerance, which may be a distance from the vector. Another example of an activity parameter value relates to acceleration. The value quantifying a level of change of motion over time in a particular direction may be associated with this parameter referenced in the activity parameter value.

Processor 80 may monitor the posture state of patient 12 and associate any therapy adjustments that patient 12 makes to the posture state currently occupied by patient 12. However, processor 80 may also employ techniques that allow a therapy adjustment to be associated with a later posture state in cases when patient 12 makes a therapy adjustment in anticipation of changing the posture state. Patient 12 may desire to make this preemptory adjustment to avoid being over-stimulated or under-stimulated after assuming the new posture state.

In some examples, processor 80 employs multiple timers that monitor therapy adjustments and when a new posture state occurs, as a result of a posture state transition. Processor 80 may use a posture search timer having a search period, where the search timer begins upon the detection of the therapy adjustment and expires when the search period lapses. The posture search timer allows a certain amount of time, or the search period, for patient 12 to finally engage in the intended posture state. In addition, processor 80 uses a posture stability timer having a stability timer, where the posture stability timer begins upon the sensing of a different posture state and requires a certain amount of time, the stability period, to elapse while patient 12 in the same posture state before the posture state can be considered the final posture state. A therapy adjustment is only associated with a posture state when the final posture state is started prior to the expiration of the search period and the final posture state lasts at least as long as the stability period. Any other therapy adjustments are either associated to the initial posture state patient 12 was engaged in when the therapy was adjusted or not associated to any posture state, depending upon the instructions stored in memory 82.

In addition to associating a therapy adjustment with a final posture state, e.g., confirmed with the aid of the search timer and posture stability timer, processor 80 may generate and associate a stability indication with the final posture state in memory 82. As discussed above, the stability indication indicates that patient 12 provided a therapy adjustment that is specific to the final posture state. The stability indication may be a flag, value or signal stored in memory 82 and associated with the final posture state.

Processor 80 also updates the therapy parameter values associated with other posture states based on the therapy adjustment provided by patient 12 for the final posture state. In particular, processor 80 updates the therapy parameter values associated with related posture states that are not correlated with a stability indication in memory 82. The absence of a stability indication associated with a particular posture state indicates that patient 12 has not provided a therapy adjustment specific to the particular posture state. For related posture states that are not associated with stability indications, at least one therapy parameter value associated therewith is a floating value that processor 80 automatically updates based on a therapy adjustment provided by patient 12 for a related posture state.

Memory 82 stores a plurality of posture states and groups the posture states into related posture states. For example, posture state module 86 may be programmed to sense a lying front posture state, a lying back posture state, a lying right posture state, and a lying left posture state, and processor 80 may identify the lying front, lying back, lying right, and lying side posture states as being related. As another example, memory 82 may store an upright posture state group that identifies an upright posture state and an upright and active posture state as being related.

The related posture state groupings may be selected by a clinician and stored in memory 82 or processor 80 may automatically determine the related posture state groupings. Patient 12 may not distinguish between the related posture states in the group and may perceive the postures as affecting the patient condition or therapy delivery in similar manners. Thus, the clinician or processor 80 may review the therapy parameter values associated with the posture states and group the posture states that have substantially similar or identical therapy parameter values together as related posture states. Therapy parameter values may be substantially similar if, for example, the values are within a threshold range of each other, e.g., the difference in the values is less than 25% or less than 10%.

In other examples, the clinician or processor 80 may identify posture states as being related based on the posture state definitions. As an example, if the posture states are defined by three-dimensional posture spaces (e.g., posture cones), the posture states associated with posture spaces having similar absolute orientations relative to a known vector (e.g., a vertical vector) may be linked as being related. For example, lying back, lying front, lying right, and lying posture cones may have similar absolute distances or angles relative to an upright vector, and, therefore, may be grouped together as related postures. In other examples, cosine values may be used to determine a posture state, and, thus, posture states may be grouped together as related posture based on the cosine values computed using a reference coordinate vector.

In some examples, programmer 20 may present a graphical user interface to a user via a display that permits the user to indicate which one or more posture states are related. The user may, for example, select the posture states for classifying in one or more groups of related posture states from a predetermined list of posture states that are presented to the user via the display.

Examples of updates to therapy parameter values that processor 80 may make for related posture states that are not associated with stability indications include, for example, applying the therapy adjustment to the therapy parameter values of the related patient posture states not associated with a stability indication. For example, processor 80 may update the therapy parameter values associated with related patient posture states such that the values are substantially equal to the therapy parameter value adjusted in response to the therapy adjustment provided by patient 12. As another example, processor 80 may apply the net change in the therapy parameter value resulting from the therapy adjustment to the therapy parameter values associated with related patient posture states. In other examples, if more than one related posture state is associated with a stability indication, processor 80 may set the therapy parameter values associated with related patient posture states that are not associated with stability indications at values substantially equal to the lowest, highest, or average value of the therapy parameter values associated with posture states associated with a stability indication.

In some examples, processor 80 updates the therapy parameter values of the related posture states in order to maintain a predetermined ratiometric balance between the therapy parameter values of the different patient posture states. Upon receiving a therapy parameter value adjustment for one posture state, processor 80 may apply the adjust to the therapy parameter values associated with related patient posture states for which no stability indication has been generated, whereby the therapy parameter value adjustment made for each of the posture states is made to maintain the relative values in a certain ratio (or proportion) to each other. As an example, processor 80 may determine that an amplitude value for the lying back posture state should be about 50% of the amplitude value of the upright posture state and an amplitude value for the lying front posture state should be about 25% of the amplitude value of the upright posture state. Thus, if the upright posture state is about 10 V, processor 80 may adjust the lying front and lying back posture states to be about 5 V and 2.5 V, respectively. Other ratiometric balances are contemplated. In addition, the therapy adjustment to maintain the ratiometric balances may be made even for posture states that are not related.

By automatically updating therapy parameter values for related posture states based on a therapy adjustment provided by patient 12 for a specific posture state, processor 80 dynamically and intelligently adapts the therapy with which stimulation generator 84 generates and delivers posture responsive therapy based on patient feedback. The automatic updates to the therapy parameter values for related posture states reflects a prediction and anticipation of efficacious therapy parameter values by processor 80 based on useful data, e.g., patient input. Because therapy delivery may have similar effects on patient 12 for each of a plurality of related posture states, a therapy adjustment for one patient posture may indicate or suggest that a similar adjustment will provide efficacious therapy to patient 12.

After each posture state in a group of related posture states is associated with a stability indication, processor 80 may stop the automatic association of one therapy adjustment to multiple posture states based on a therapy adjustment for one posture state. While patient 12 may continue making therapy adjustments for a specific posture state, processor 80 may only update a sensed posture state with the therapy adjustment.

In other examples, a processor of external programmer 20 may perform any part of the programming techniques described herein, such as the automatic association of a therapy adjustment with multiple related posture states. Any shared processing between IMD 14 and external programmer 20 is contemplated.

IMD 14 wirelessly communicates with external programmer 20, e.g., patient programmer 30 or clinician programmer 60, or another device via radio frequency (RF) communication or proximal inductive interaction of IMD 14 with external programmer 20. For example, processor 80 may transmit therapy adjustments and associated posture state information to programmer 20 for later analysis by a clinician. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply could transcutaneously power IMD 14 when needed or desired.

Figure 5:
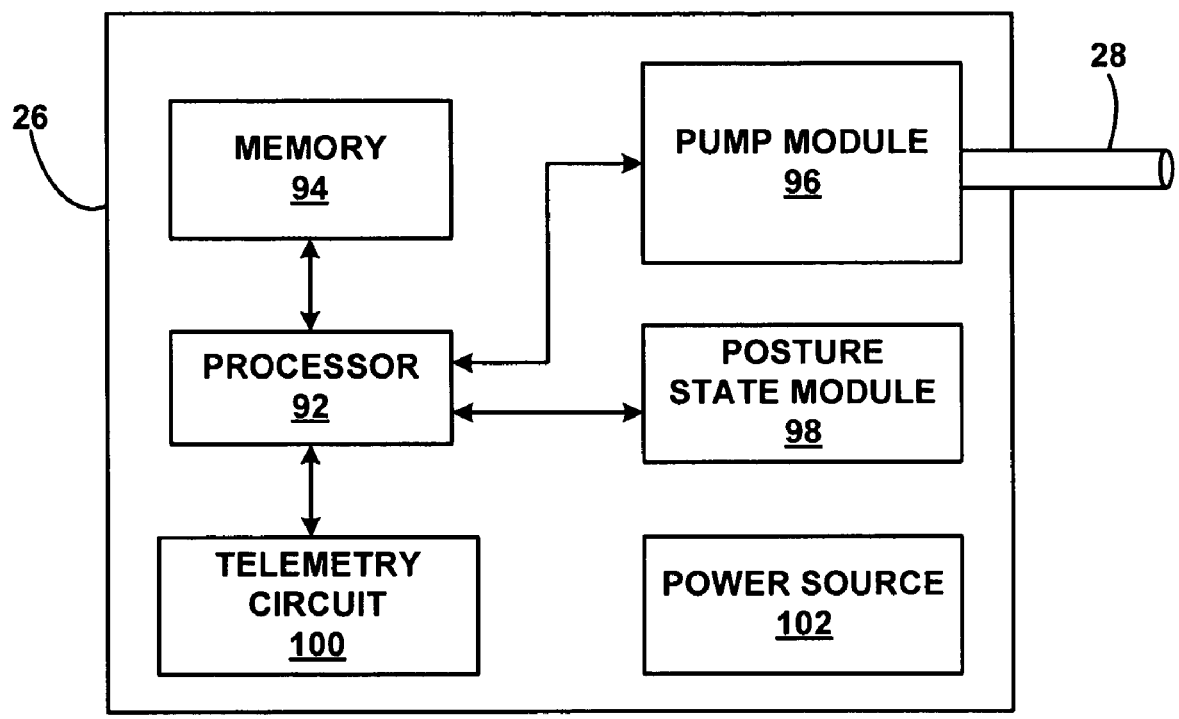
FIG. 5 is a functional block diagram illustrating various components of an implantable drug pump.

FIG. 5 is a functional block diagram illustrating various components of an IMD 26, which delivers a therapeutic agent to patient 12. IMD 26 is a drug pump that operates substantially similar to IMD 14 of FIG. 4, but delivers a therapeutic agent instead of electrical stimulation. IMD 26 includes processor 92, memory 94, pump module 96, posture state module 98, telemetry circuit 100, and power source 102. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 controls pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state 98 to adjust drug delivery therapy when patient 12 changes posture states.

Figure 6:
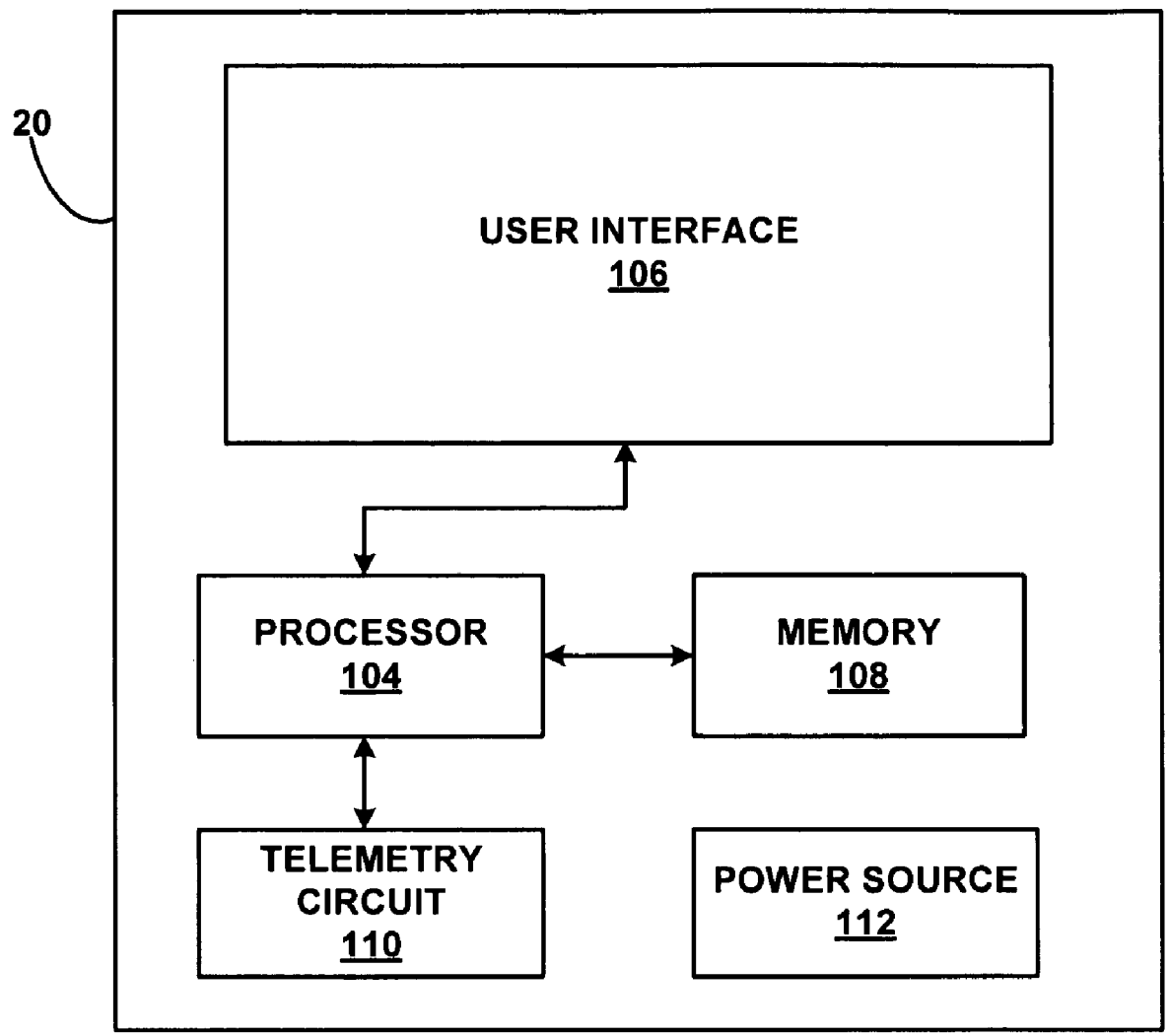
FIG. 6 is a functional block diagram illustrating various components of an external programmer for an implantable medical device.

FIG. 6 is a functional block diagram illustrating various components of an external programmer 20 for IMDs 14 or 26. As shown in FIG. 6, external programmer 20 includes processor 104, memory 108, telemetry circuit 110, user interface 106, and power source 112. External programmer 20 may be embodied as patient programmer 30 or clinician programmer 60. A clinician or patient 12 interacts with user interface 106 in order to manually change the stimulation parameters of a program, change programs within a group, turn posture responsive stimulation ON or OFF, view therapy information, view posture state information, or otherwise communicate with IMDs 14 or 26.

User interface 106 may include a screen and one or more input buttons, as in the example of patient programmer 30, that allow external programmer 20 to receive input from a user. Alternatively, user interface 106 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Input buttons for user interface 106 may include a touch pad, increase and decrease buttons, emergency shut off button, and other buttons needed to control the stimulation therapy, as described above with regard to patient programmer 30. Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to patient therapy.

User interface 106 is configured to present therapy adjustment information to the user for monitoring adjustments made by patient 12 and allowing single input and guided programming options for the user. After IMD 14 has associated therapy adjustments to posture states, user interface 106 of external programmer 20 may present the associations to the user as a range of therapy adjustments, maximum and minimum values of the adjusted parameters, last adjustments made, number of adjustments made for each program and posture state, or any other details relating to posture states and therapy adjustments, as described by U.S. Patent Application Publishing No. 2010/0010588 by Skelton et al. User interface 106 may also present information related to posture states associated with stability indications, posture states that are identified as being related, and adjustments made to related posture states in response to the therapy adjustment provided by patient 12. In addition, user interface 106 may display the therapy adjustment information as graphical bar graphs or charts, numerical spread sheets, or any other manner in which information may be displayed. Further, user interface 106 may present nominal or suggested therapy parameters that the user may accept for all programs by making one confirmation input to user interface 106.

The therapy adjustment information may also be stored within memory 108 periodically during therapy, whenever external programmer 20 communicates within IMD 14, or only when the user desired to use the therapy adjustment information. Memory 108 may include a separate memory for therapy adjustment information as opposed to other posture state information or operational instructions. In addition, if memory 108 does store posture state information from patient 12, memory 108 may use one or more hardware or software security measures to protect the identify of patient 12. For example, memory 108 may have separate physical memories for each patient or the user may be required to enter a password to access each patient's posture state data.

Telemetry circuit 110 allows the transfer of data to and from IMD 14 or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 14 in addition to programming IMD 14. Alternatively, a recharging device may be capable of communication with IMD 14. Then, the recharging device may be able to transfer programming information, data, or any other information described herein to IMD 14. In this manner, the recharging device may be able to act as an intermediary communication device between external programmer 20 and IMD 14. The techniques described herein may be communicated between IMD 14 via any type of external device capable of communication with IMD 14.

Processor 104 comprises one or more microprocessors, DSPs, ASICs, FPGAs, programmable logic circuitry, or the like, either alone or in any suitable combination. The functions attributed to 104 described herein may be provided by a hardware device and embodied as software, firmware, hardware, or any combination thereof associated with such a hardware device. Processor 104 of programmer 20 may perform any part of the techniques described above with respect to programmer 80 of IMD 14.

Figure 7:
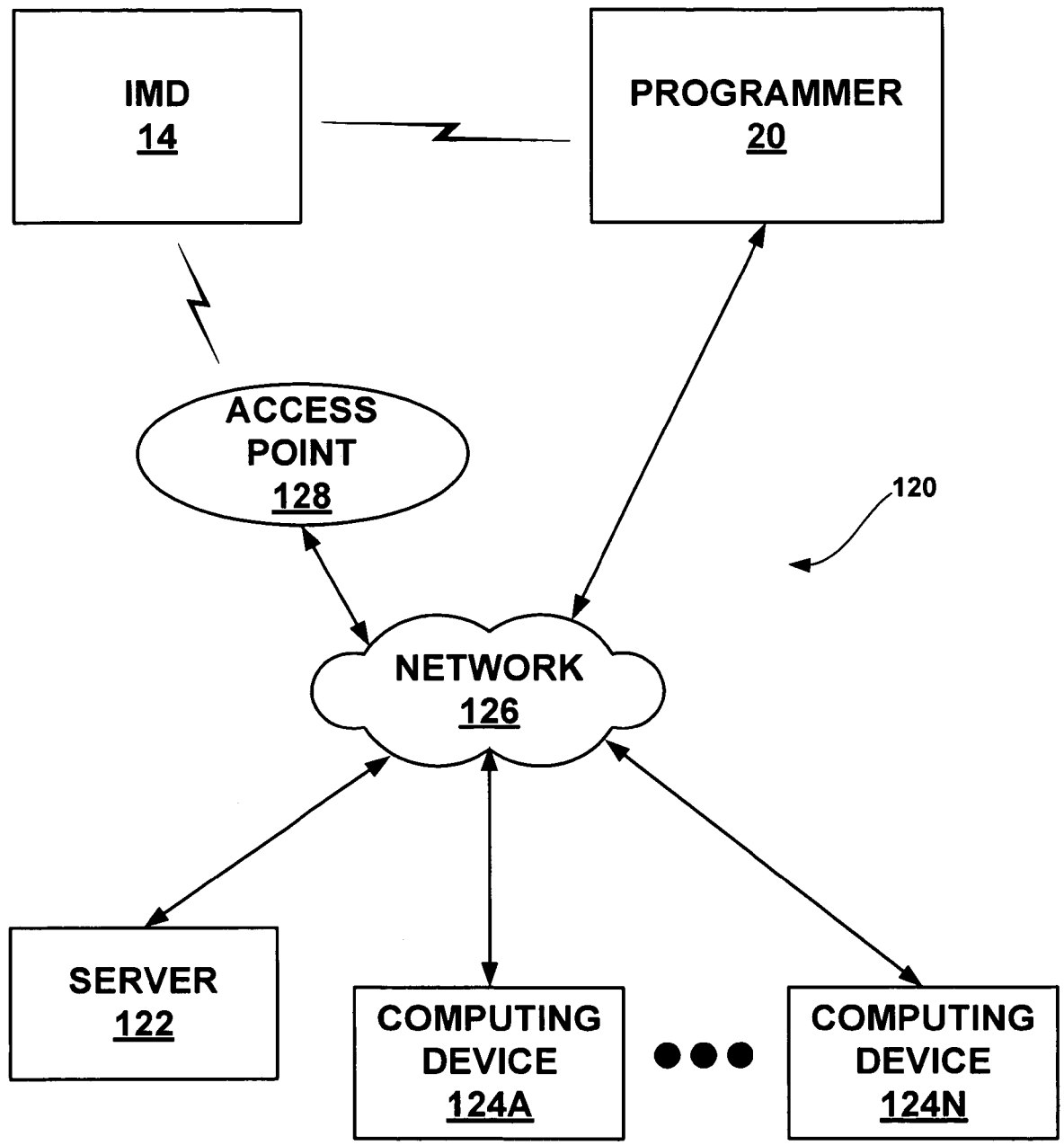
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 to communicate with external programmer 20 via a first wireless connection, and to communication with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, DSPs, ASICs, FPGAs, programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other embodiments, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day. In some cases, IMD 14 may directly analyze the collected data to evaluate the posture state of patient 12, such as what percentage of time patient 12 was in each identified posture. In other cases, however, IMD 14 may send stored data relating to posture state information to external programmer 20 and/or server 122, either wirelessly or via access point 128 and network 126, for remote processing and analysis. For example, IMD 14 may sense, process, trend and evaluate the sensed posture state information. This communication may occur in real time, and network 126 may allow a remote clinician to review the current patient posture state by receiving a presentation of a posture state indication on a remote display, e.g., computing device 124A. Alternatively, processing, trending and evaluation functions may be distributed to other devices such as external programmer 20 or server 122, which are coupled to network 126. In addition, posture state information may be archived by any of such devices, e.g., for later retrieval and analysis by a clinician.

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 122. A clinician or other trained professional may review and/or annotate the posture state report, and possibly identify any problems or issues with the therapy that should be addressed. Further, server 122 may process therapy adjustment information and generate suggested therapy parameters for each program and posture state based upon the therapy adjustment information. If a guided algorithm is computationally intensive, server 122 may be best suited for generating the necessary parameters for therapy.

Using the system shown in FIG. 7, a clinician, physician, technician, or even patient 12, may review therapy adjustment information from the record mode of IMD 14. The user may remotely monitor the progress and trends of patient 12, limiting the number of times that patient 12 may need to physically visit the clinician. This monitoring may also reduce the time needed to find efficacious therapy parameters by allowing the clinician to more frequently monitor how patient 12 is using patient programmer 30 and how often changes to therapy must be made. Any of the user interfaces described herein with respect to patient programmer 30 or clinician programmer 60 may also be presented via any of computing devices 124A-124N.

In some cases, server 122 may be configured to provide a secure storage site for archival of posture state information that has been collected from IMD 14 and/or external programmer 20. Network 126 may comprise a local area network, wide area network, or global network, such as the Internet. In some cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients. Further, posture state detection may also be used to provide notifications, such as providing notification via a wireless link to a care giver that a patient has potentially experienced a fall.

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12. For example, if the output of one or more posture state sensors is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state sensor, e.g., a three-axis accelerometer that provides data indicating the posture state of patient 12, to sense posture vectors. A sense vector may be determined based on the output of the posture state sensor (e.g., based on the x, y, and/or z outputs from one or more single axis, two-axis or three-axis accelerometers). While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side of the body. For example, a lying right posture cone and a lying left posture cone positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to patient programmer 30 so that the patient programmer can present a posture state indication to patient 12.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient was occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of 80 degrees, +40 degrees to −40 degrees from the positive vertical axis 141. In some cases, lying cones may be defined relative to the reference coordinate vector of the upright cone 142. For example, lying up cone 148 may have an angle of 80 degrees, −50 degrees to −130 degrees from the positive vertical axis 141. Inverted cone 146 may have an angle of 80 degrees, −140 degrees to +140 degrees from vertical axis 141. In addition, lying down cone 144 may have an angle of 80 degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from the posture state sensor is placed in relation to the posture cones. Posture state space 152 is substantially similar to posture state area 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A. The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cone 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut or toroid-like volume and the volumes of the lying posture cones. If the cones are larger such that some portions extend beyond the lying volume, then those portions can be added to the lying volume using the logical OR-like operation.

If the sensed coordinate vector resides within the donut or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E" may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone.

The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one or more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 86 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 86 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20. In some examples, the posture states that are grouped together in this manner may be treated as group of related posture states for purposes of therapy parameter value adjustments, e.g., using the technique described with respect to FIG. 18.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

Figure 9:
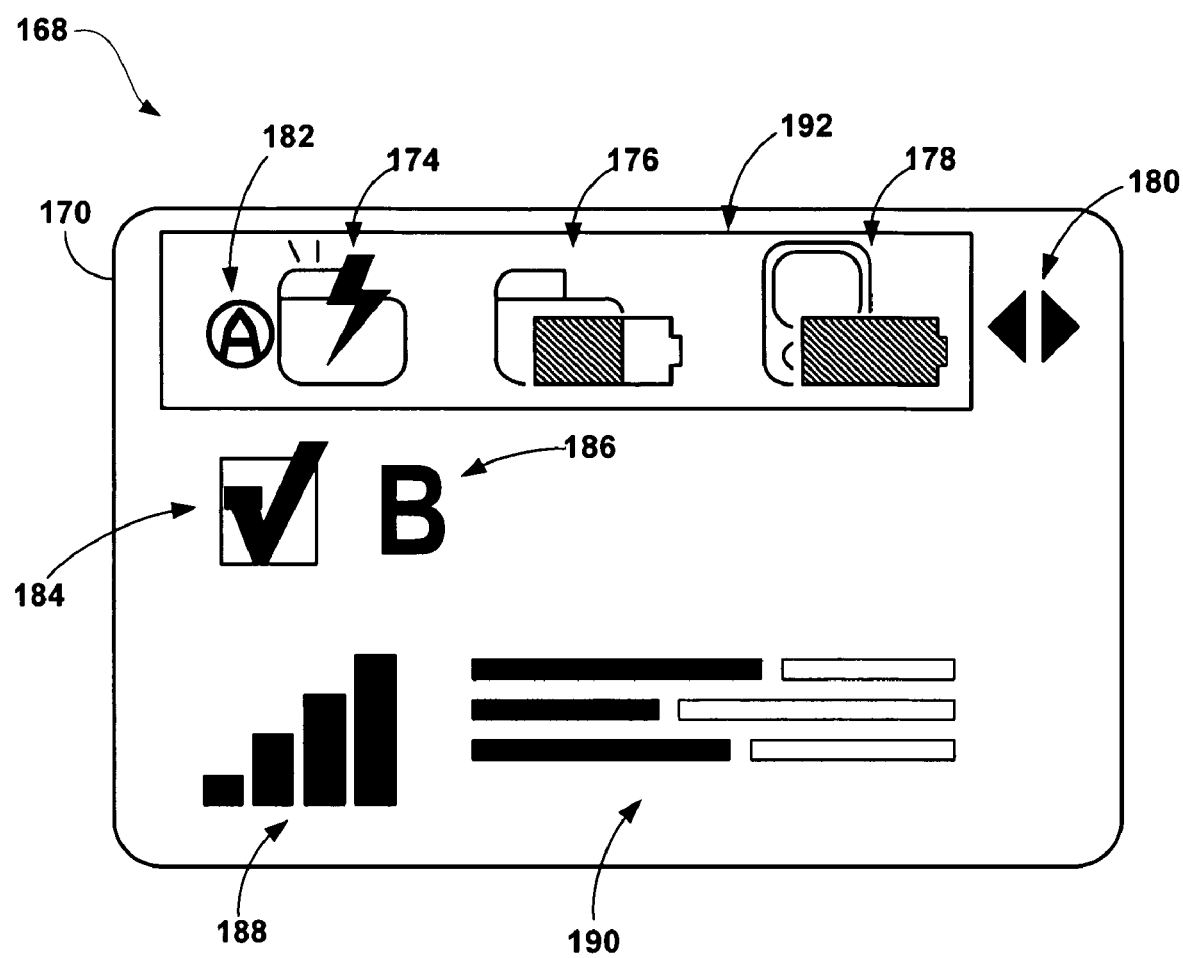
FIG. 9 is a conceptual illustration of an example user interface of a patient programmer that presents therapy information to the patient.

FIG. 9 is a conceptual diagram illustrating an example user interface 168 of a patient programmer 30 for delivering therapy information to patient 12. In other examples, a user interface similar to user interface 168 may also be presented by clinician programmer 60. In the example shown in FIG. 9, display 36 of patient programmer 30 presents user interface 168 to the user, such as patient 12, via screen 170. Screen 170 includes stimulation icon 174, IMD battery icon 176, programmer battery icon 178, navigation arrows 180, automatic posture response icon 182, group selection icon 184, group identifier 186, program identifier 188, amplitude graph 190, and selection box 192. User interface 168 provides information to patient 12 regarding therapy group, therapy program, amplitude, and automatic posture response status. User interface 168 may be configurable, such that more or less information may be provided to patient 12, as desired by the clinician or patient 12.

Selection box 192 allows patient 12 to navigate to other screens, groups, or programs using navigation arrows 180 to manage the therapy. In the example of screen 170 shown in FIG. 9, selection box 192 is positioned so that patient 12 may use arrows 44 and 48 (FIG. 2) of user input mechanism 40 of programmer 30 to move between an automatic posture response screen, a volume screen, a contrast or illumination screen, a time screen, and a measurement unit screen of patient programmer 30. In these screens, patient 12 may be able to control the use of the automatic posture response feature and adjust the patient programmer features. Patient 12 may only adjust the features presented within selection box 192.

Group identifier 186 indicates one of possibly several groups of programs that can be selected for delivery to patient 12. Group selection icon 184 indicates whether the displayed group, e.g., group B in FIG. 9, is actually selected for delivery to patient 12. If a presently displayed group is selected, group selection icon 184 includes a box with a checkmark. If a presently displayed group is not selected, group selection icon 184 includes a box without a checkmark. To navigate through stored therapy program groups, a user may use control pad 40 (FIG. 2) of programmer 30 to move selection box 192 to select the group identifier 186 and then use control pad 40 to scroll through the various groups, e.g., A, B, C, and so forth. IMD 14 may be programmed to support a small number of groups or a large number of groups, where each group contains a small number of programs or a large number of programs that are delivered simultaneously, in sequence, or on a time-interleaved basis.

For each group, group selection icon 184 indicates the appropriate status. For a given group, program identifier 188 indicates one of the programs associated with the group. In the example shown in FIG. 9, no program number is indicated by program identifier 188 because all of the programs' amplitudes are shown in each bar of amplitude graph 190. Solid portions of the bars indicate the relative amplitude IMD 14 currently is using to deliver stimulation therapy to patient 12, while open portions of the bars indicate the remaining amplitude available to each program. In some examples, numerical values of the amplitude for each program may be show in addition to or in place of amplitude graph 190. In other examples of user interface 168 specific to drug delivery using IMD 26, amplitude graph 190 may show the flow rate of drugs or frequency of bolus delivery to patient 12. This information may be show in numerical format as well. Patient 12 may encompass group selection icon 184 with selection box 192 to scroll between the different programs of the selected group.

Automatic posture response icon 182 indicates that a posture responsive therapy mode of IMD 14 is activated, such that processor 80 (FIG. 4) of IMD 14 automatically adjusts therapy to patient 12 based upon the posture state detected by posture state module 86 (FIG. 4). In particular, when the posture responsive therapy mode of IMD 14 is activated, processor 80 may automatically adjust therapy delivery to patient 12 based on a detected patient posture by adjusting one or more therapy parameter values, selecting different programs or selecting different program groups based on the detected posture state of the patient. In the user interface shown in FIG. 9, automatic posture response icon 182 is not present next to group identifier 186, indicating that for therapy program group "B," IMD 14 does not provide posture responsive therapy to patient 12.

Some groups or individual programs in groups may support automatic posture responsive therapy when the posture responsive therapy mode of IMD 14 is activated. For example, automatic adjustment of one or more therapy parameter values in response to posture state indication may be selectively activated or deactivated based on settings entered by a clinician, or possibly patient 12. Hence, some therapy programs or groups may be configured for use with posture responsive therapy while other programs or groups may not be configured for use with posture responsive therapy, despite posture responsive therapy mode of IMD 14 being activated. In some cases, if posture responsive therapy supported by the automatic posture response feature is desired, patient 12 may need to switch therapy to a different group that has automatic posture responsive therapy activated for IMD 14 to adjust therapy according to the patient posture state.

Figure 10:
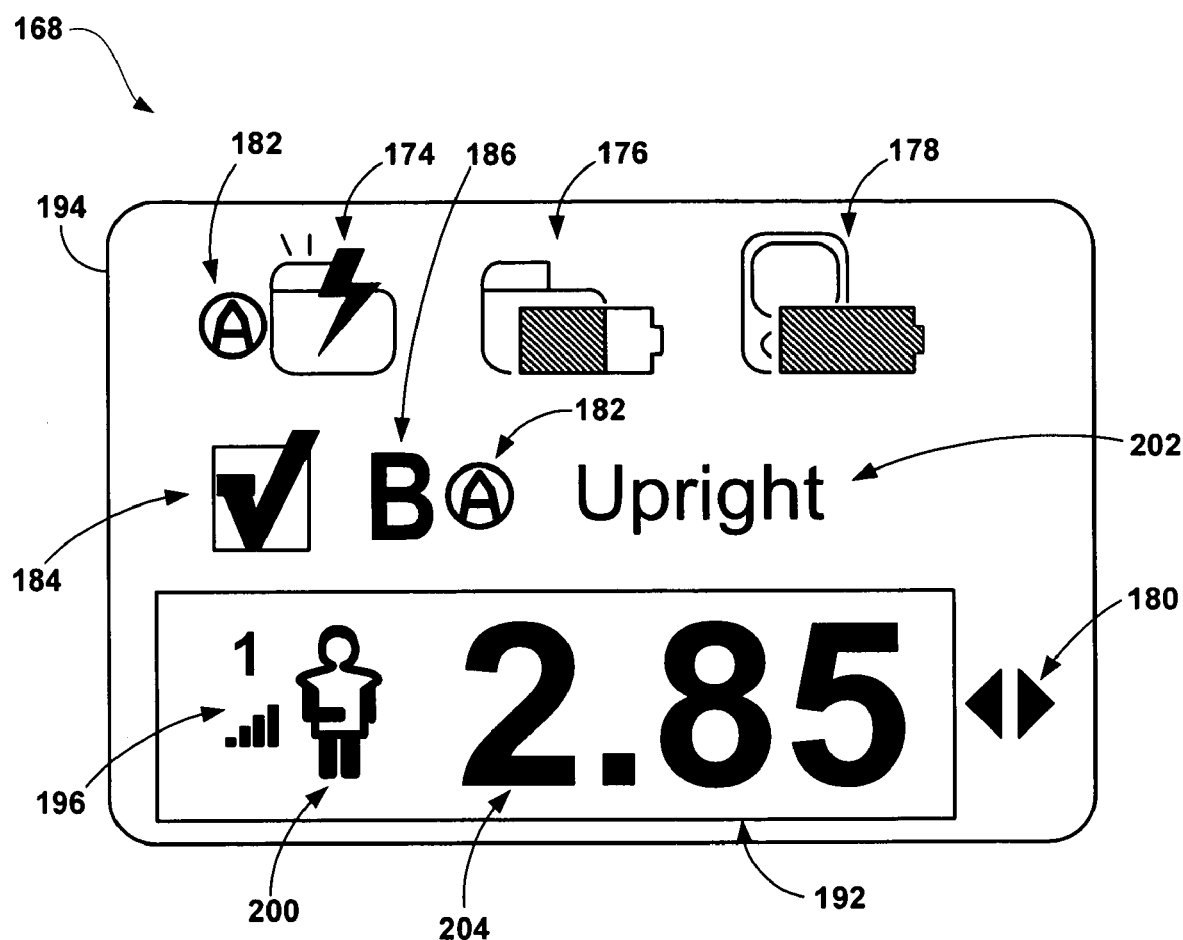
FIG. 10 is a conceptual illustration of an example user interface of a patient programmer that presents therapy information including posture information to the patient.

FIG. 10 is a conceptual diagram illustrating an example user interface 168 of a patient programmer 30 for delivering therapy information that includes posture information to the patient. In other examples, user interface 168 may also be shown on clinician programmer 60. In the example of FIG. 10, display 36 of patient programmer 30 provides user interface 168 to the user, such as patient 12, via screen 194. Just as with screen 170 of FIG. 9, screen 194 presents stimulation icon 174, IMD battery icon 176, programmer battery icon 178, and automatic posture response icon 182. In addition, screen 194 includes group selection icon 184, group identifier 186, supplementary posture state indication 202, program identifier 196, posture state indication 200, amplitude value 204, selection box 192, and selection arrows 180. User interface 168 provides information to patient 12 regarding a therapy group, therapy program, stimulation amplitude, automatic posture response status (e.g., an indication of whether the posture responsive therapy mode of IMD 14 is activated), and posture state information. More or less information may be provided to patient 12, as desired by the clinician or the patient.

Group identifier 186 indicates that therapy group "B" is active, and automatic posture response icon 182 indicates group "B" (containing one or more programs) is activated to allow IMD 14 to automatically adjust therapy according to the patient posture state. In the example shown in FIG. 10, user interface 168 indicates the posture state determined by IMD 14, e.g., via posture state indication 200 and supplementary posture state indication 202. Program identifier 196 illustrates that information regarding program "1" of group "B" is displayed on screen 194. In the example shown in FIG. 10, an amplitude value 204 illustrating the current voltage amplitude of program "1" of 2.85 Volts is presented to the user. Patient 12 (or another user) may scroll through different programs of the group by using navigation arrows 180 via arrows 44 and 48 of control pad 40 (FIG. 2).

Posture state indication 200 shows that IMD 14 is detecting that patient 12 is in the upright or standing posture based on posture state module 86 (FIG. 4). Supplementary posture state indication 202 supplements posture state indication 200 by providing a textual indication of the exact posture being detected by posture state module 86 of IMD 14. Posture state indication 200 and supplementary posture state indication 202 presented via user interface 168 change according to the sensed, or detected, posture state detected by IMD 14. The posture state may be communicated to external programmer 20 substantially immediately after IMD 14 detects a posture change, periodically communicated to programmer 20, or non-periodically communicated by IMD 14 unilaterally or upon receiving a request from programmer 20. Accordingly, the posture state indication 200 and/or supplementary posture state indication 202 may represent a current, up-to-the minute status (e.g., a real-time patient posture state), or a status as of the most recent communication of posture state from IMD 14. Posture state indication 200 is shown as a graphical representation, but the posture state indication may alternatively be presented as any one of a symbolic icon, a word, a letter, a number, an arrow, or any other representation of the posture state. In some cases, posture state indication 200 may be presented without supplementary posture state indication 202.

Selection box 192 indicates that patient 12 view other programs within group "B" using selection arrows 180. Selection box 192 may be moved to select other screen levels with control pad 40 of programmer 20 (FIG. 2) in order to navigate through other stimulation groups or adjustable elements of the therapy. When patient 12 selects a different program with control pad 40, program identifier 196 is updated to correctly identify the current program viewed on screen 194.

In addition to graphical, textual or other visible indications of posture state, the external programmer may present audible and/or tactile indications of posture state via any of a variety of audible or tactile output media. An audible indication may be spoken words stating a posture state, or different audible tones, different numbers of tones, or other audible information generated by the programmer to indicate posture state. A tactile indication may be, for example, a somatosensory indication, such as a different numbers of vibratory pulses delivered in sequence or vibratory pulses of different lengths, amplitudes, or frequencies.

Figure 11:
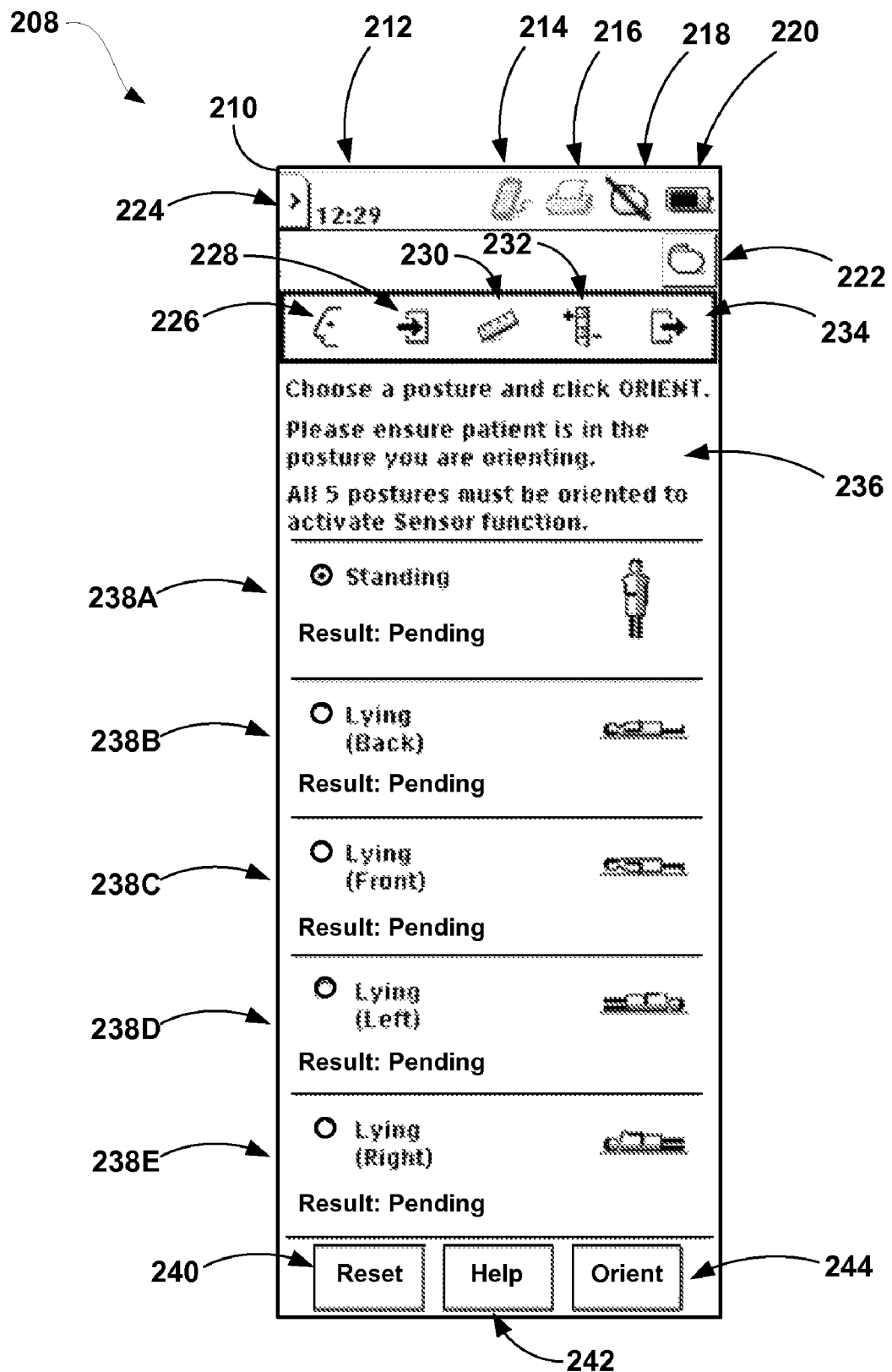
FIG. 11 is a conceptual diagram illustrating an example user interface for orienting the implantable medical device.

FIG. 11 is a conceptual diagram illustrating an example user interface 208 for orienting IMD 14 device prior to diagnostic or therapy use. User interface 208 is described as generally being displayed by clinician programmer 60. However, user interface 208 may also be displayed by patient programmer 30 or some other external programmer 20 or remote device. In any case, user interface 208 displays information related to sensing posture states, automatic posture response, reviewing recorded therapy adjustment information, and suggested therapy parameters to increase therapy efficacy.

A clinician may interact with user interface 208 to determine posture state definitions for patient 12 upon initial implantation of IMD 14 or periodically throughout the use of IMD 14 to provide chronic therapy to patient 12. In the example shown in FIG. 11, screen 210 of user interface 208 presents networking icon 214, printer icon 216, IMD communication icon 218, programmer battery icon 220, stimulation status icon 222, operational menu 224, patient data icon 226, data recording icon 228, device status icon 230, programming icon 232, data reporting icon 234, and orientation information 236. In addition, screen 210 of user interface 208 includes posture state selections 238A, 238B, 238C, 238D, and 238E (collectively "posture state selections 238"), reset button 240, help button 242, and orient button 244. In some examples, screen 210 may not include some features, such as the help button 242.

Screen 210 may be accessed by selecting programming icon 232 to access a drop down menu that allows the user to select one of multiple different screens. The user may select "orient device" or some other text or icon that symbolizes access to the process for initializing the orientation of the posture state sensor within IMD 14.

Specific to screen 210 of user interface 208, the clinician may initialize the orientation of the posture state sensor of IMD 14 by helping patient 12 assume each of posture state selections 238A-238E and determining the output of the posture state sensor of posture state module 86 (FIG. 4) of IMD 14 to that particular posture state selection. Orient information 236, while not necessary in all examples, provides instructions to the clinician relating to how to orient IMD 14 to patient 12. For example, FIG. 11 shows that the clinician has selected posture state selection 238A. Once patient 12 has assumed the standing position, the clinician selects orient button 244 to have IMD 14 associate the posture state sensor output to the standing posture state in memory 82 (FIG. 4). Clinician programmer 60 may also store the posture state sensor output information. The clinician may repeat this process for each of posture state selections 238A-238E, in any order that the clinician chooses.

In other examples, the clinician may not need to orient IMD 14 to each of the five posture state selections 238A-238E. For example, IMD 14 may only require three posture state selections, such as standing, one of lying back or lying front, and one of lying left and lying right. The lying back and lying front posture states may have a predetermined relationship to each other such that the definition of one of the lying back or lying front posture states may be used to determine the other posture state. Similarly, the lying left and lying right posture states may have a predetermined relationship to each other such that the definition of one of the lying right or lying left posture states may be used to determine the other posture state. Other relationships between posture states may also be used to orient IMD 14 to each of a plurality of posture states, which may, but need not be, the posture states shown in FIG. 11.

Orienting IMD 14 may be a necessary step before IMD 14 is capable of accurately sensing or detecting any posture state engaged by patient 12. Therefore, user interface 208 may prevent the clinician from entering the record mode, for example, unless the clinician has oriented IMD 14 to patient 12. In this manner, any recorded associations between therapy adjustments and posture states or automatic posture response therapy is completed appropriately.

Screen 210 of user interface 208 includes multiple menus and icons common to other screens of user interface 208 provided by clinician programmer 60 for programming therapy provided by IMD 14. Operational menu 224 is a button that the user may select to view multiple options or preferences selectable by the user. Operational menu 224 may provide preferences for clinician programmer 60 instead of therapy specific information. Networking icon 214 is shown as grayed out to indicate that clinical programmer 60 is not currently connected to a network. When networking icon 214 is shown fully, clinician programmer 60 is connected to a network. Printer icon 216 indicates when clinician programmer 60 is connected to a printer. When printer icon 216 is grayed out as shown in FIG. 11, there is no printer connected to clinician programmer 60.

Further, IMD communication icon 218 is shown as indicating that clinician programmer is not in communication with IMD 14 because the icon includes a slash through the IMD representation. The slash is removed when clinician programmer 60 has established a communication link to IMD 14. In addition, programmer battery icon 220 indicates the current charge level of the battery contained within clinician programmer 60. Stimulation status icon 222 indicates to the user when stimulation is being delivered to patient 12. Stimulation is not currently being delivered, but stimulation status icon 222 may include an electrical bolt through the IMD representation when stimulation is delivered.

Screen 210 also provides menu options related to stimulation therapy of patient 12. Patient data icon 226 allows the user to enter and review data related to the status of and the condition of patient 12. Data recording icon 228 allows the user to navigate to other screens to enter data recording preferences and review stored data. Device status icon 230 allows the user to view operational status of components of IMD 14, such as electrodes, leads, batteries, and any discovered problems. Programming icon 232 allows the user to navigate to programming screens that define the stimulation therapy parameters used to deliver stimulation to patient 12. In addition, data reporting icon 234 allows the user to view and print reports of patient progress and other therapy information.

Figure 12:
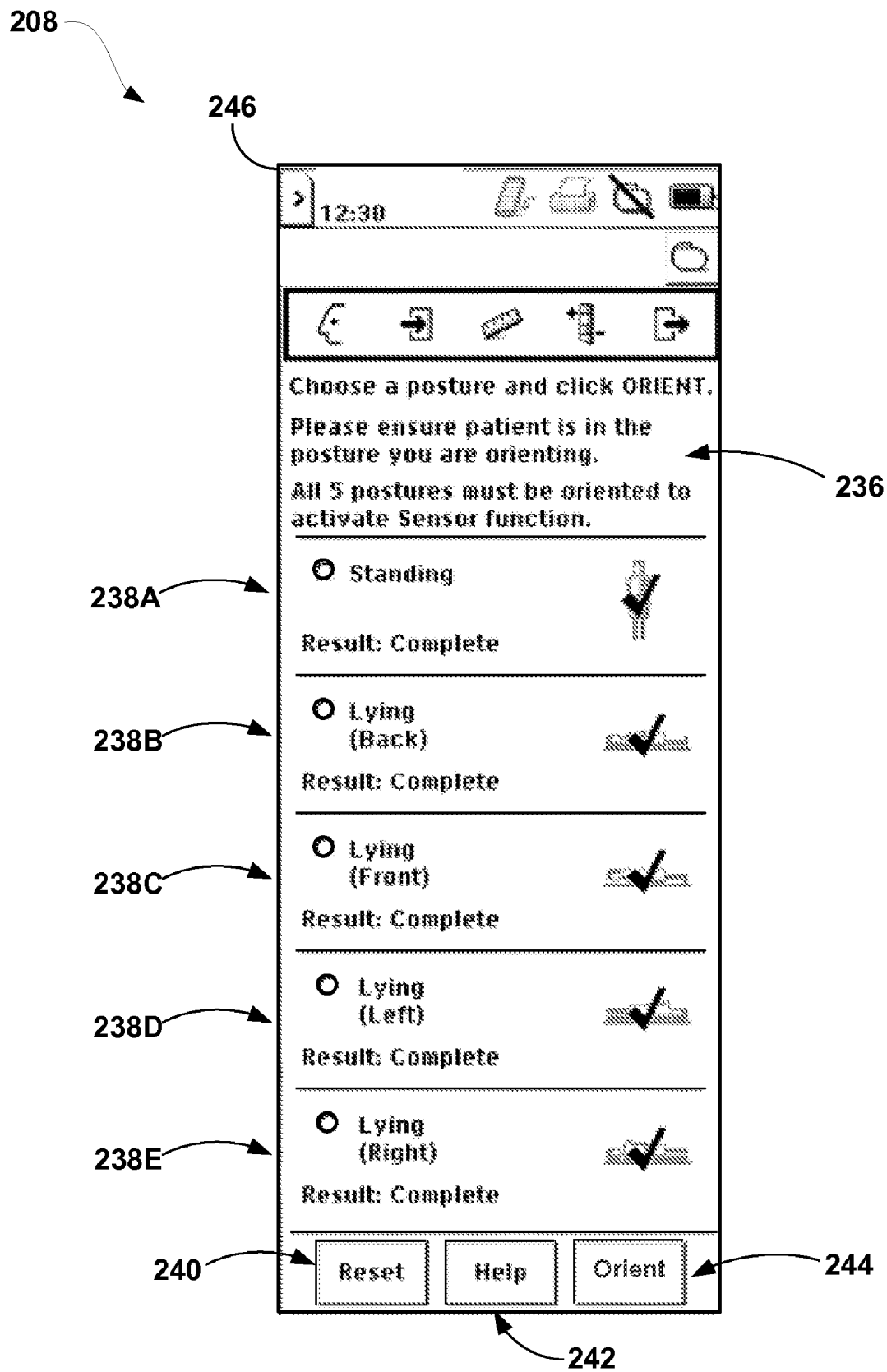
FIG. 12 is a conceptual diagram illustrating an example user interface showing the user that orientation of the implantable medical device is complete.

FIG. 12 is a conceptual diagram illustrating an example user interface 208 showing the user that orientation of the implantable medical device is complete. As shown in FIG. 12, screen 246 of user interface 208 indicates to the clinician that orientation of IMD 14 has been completed for each of the posture state selections 238 as described in FIG. 11. Each of the posture state selections 238 has a check mark through the graphical posture state indication on the right side of screen 246 to indicate that each posture state selection 238 has been oriented. Further, orient button 244 has been grayed out so that the clinician cannot select it. Once clinician programmer 60 is presented with screen 246, the clinician may move on to start the record mode, select therapy programs for each posture state, or any other programming task that requires sensing of the posture state of patient 12. In alternative examples, clinician programmer 60 may automatically begin the record mode and any other posture state related applications once IMD 14 has been oriented to patient 12. For example, objectification and record modes may be automatically turned on once the orientation process is completed.

Figure 13:
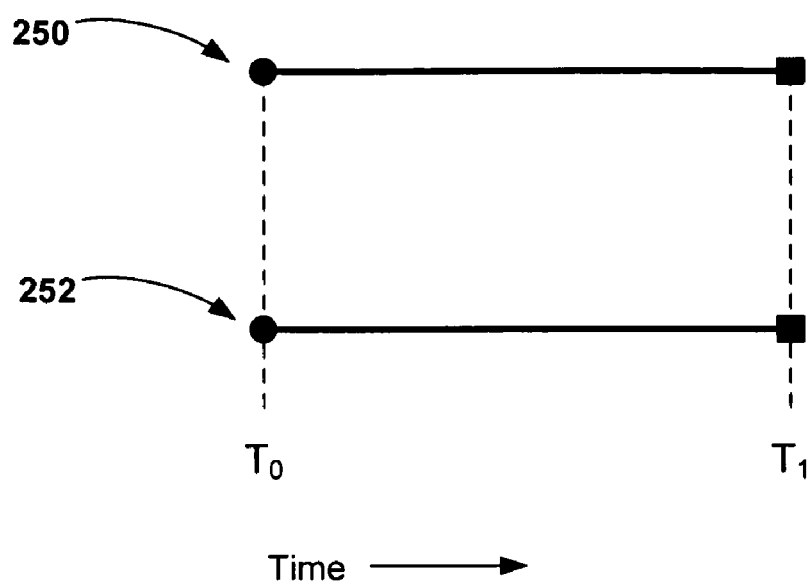
FIG. 13 is a conceptual diagram illustrating example posture search and posture stability timers with one posture state.

FIG. 13 is a conceptual diagram illustrating example posture search timer 250 and posture stability timer 252, which may be used to determine when patient 12 remains in one posture state. As mentioned previously, it is desirable for IMD 14 to correctly associate each therapy adjustment to a therapy parameter to the intended posture state of patient 12 when the therapy adjustment was made. For example, patient 12 may make therapy adjustments to customize the therapy either after patient 12 transitions to a different posture state or in anticipation of the next posture state (e.g., a prospective posture state). Processor 80 of IMD 14 may employ posture search timer 250 and posture stability timer 252 to track therapy adjustments and the current posture state of patient 12. Although processor 80 may associate therapy adjustments to any therapy parameter to a posture state, some examples of IMD 14 may only allow the association of amplitude changes. In this manner, patient 12 may adjust values for different therapy parameters, such as pulse width, pulse rate, or electrode configuration, but IMD 14 will not store these therapy adjustments as being associated to any posture state.

Posture search timer 250 defines a search period for patient 12 to transition posture states to a final posture state following a therapy adjustment. Posture search timer 250 begins at the time patient 12 provides the therapy adjustment and may restart with each therapy adjustment. In this way, the search period defined by posture search timer 250 indicates a fixed amount of time, starting from the time at which a patient provided the therapy adjustment, during which patient 12 must assume a final, stable posture state in order for the therapy adjustment to be associated with the final posture state. If patient 12 does not transition to the final posture state prior to the expiration of the search period defined by posture search timer 250, processor 80 (FIG. 4) of IMD 14 does not automatically associate the therapy adjustment with the final posture state.

Posture stability timer 252 defines a stability period during which patient 12 must maintain the final posture state before processor 80 automatically associates the therapy adjustment with the final posture state. That is, posture stability timer 252 sets the amount of time that patient 12 must remain within the final posture state before the therapy adjustment will be associated with the final posture state. Posture stability timer 252 restarts with each posture state transition made by patient 12, i.e., each detection of a new posture. The search period and stability period must overlap in order for processor 80 to associate a therapy adjustment with a posture state not currently engaged by patient 12 when the therapy adjustment was made.

In the example shown in FIG. 13, patient 12 makes a therapy adjustment to one of the therapy parameters, such as voltage or current amplitude, at time $T_0$, while patient 12 is in a first posture state. Posture search timer 250 starts when a therapy adjustment is made by patient 12. Thus, as shown in FIG. 13, posture search timer 250 starts at $T_0$ and runs for a predetermined search period, which expires at time $T_1$. Posture stability timer 252 also starts when patient 12 makes the therapy adjustment (at time $T_0$) and while patient 12 in the first posture state. Posture stability timer 252 continues to run for a predetermined stability period, which is equal in duration to the search period in the example shown in FIG. 13. In the example shown in FIG. 13, patient 12 does not change posture states between times $T_0$ and $T_1$, and, therefore, the stability period ends at time $T_1$, i.e., upon expiration of the stability period. The therapy adjustment made by patient 12 at time $T_0$ is associated with the first posture state sensed by posture state module 86 (FIG. 4) of IMD 14 between times $T_0$ and $T_1$ because both the search period and stability period overlap.

In some examples, the search period defined by posture search timer 250 may be of any time duration desired by the manufacturer, and the clinician may or may not be permitted to set or modify the search period. Generally, the search period may be between about one minute and about 60 minutes, such as about 30 seconds to about 30 minutes, but it may be set to any time desired, including a time that is outside of that range. For example, the search period may be between about 30 seconds to about five minutes or about two minutes to about three minutes in order to provide a reasonable amount of time for patient 12 to be engaged in the final desired posture state with which the therapy adjustment should be associated. In some examples, and as described in the examples of FIGS. 13-17, the search period is approximately three minutes.

In addition, the stability period defined by posture stability timer 252 may be of any suitable duration, which may be selected by the manufacturer or clinician. The clinician may or may not be permitted to set or modify the stability period. Generally, the stability period is between about one minute and about 60 minutes, such as about 30 seconds to about 30 minutes, but it may be set to any time desired, including times outside of that range. More specifically, the stability period may be between 30 seconds to about five minutes, such as about two minutes to about three minutes in order to ensure that patient 12 engaged in the final desired posture state for a reasonable amount of time and that the final posture state is not a transitional or interim posture state. In some examples, and as described in the examples of FIGS. 13-17, the stability period is approximately three minutes. Although the search period and stability period have the same duration in the example shown in FIG. 13, in other examples, the search period and stability period may be different.

As described herein, associating therapy adjustments with intended posture states allows a clinician (or another user) to review the types of therapy adjustments patient 12 has made while assuming, or transitioning to, each posture state. However, the associations may also be used to update therapy parameter values (e.g., as defined by programs or groups) that define the stimulation therapy delivered to patient 12, instead of, or in addition to, simply storing the associations for later review. For example, with the aid of timers 250, 252, processor 80 of IMD 14 may determine that a therapy adjustment made by patient 12, while in a first posture, to increase the amplitude of the current program is associated with a second, subsequent posture state assumed by patient 12.

Processor 80 may then update the therapy program associated with the second posture state based on the therapy adjustment. For example, processor 80 may update the therapy program to reflect the increased amplitude. In this case, the next time patient 12 engages in the second posture state, IMD 14 will automatically deliver stimulation therapy according to the increased amplitude made by patient 12. Therefore, IMD 14 may use posture search timer 250 and posture stability timer 252 to learn or update program therapy parameters such that IMD 14 remembers the therapy parameters for therapy delivery for subsequent delivery according to the engaged posture state.

In addition, processor 80 also associates the second posture state with a stability indication upon associating the therapy parameter adjustment with the therapy program. Posture states associated with stability indications in memory 82

(FIG. 4) of IMD 14 indicate that patient 12 provided a therapy adjustment specific to the respective posture state. As discussed above, processor 80 also updates therapy parameter values for posture states related to the second posture state and not associated with stability indications. Examples of updates to therapy parameter values for related posture states are described in further detail with reference to FIG. 18.

Figure 14:
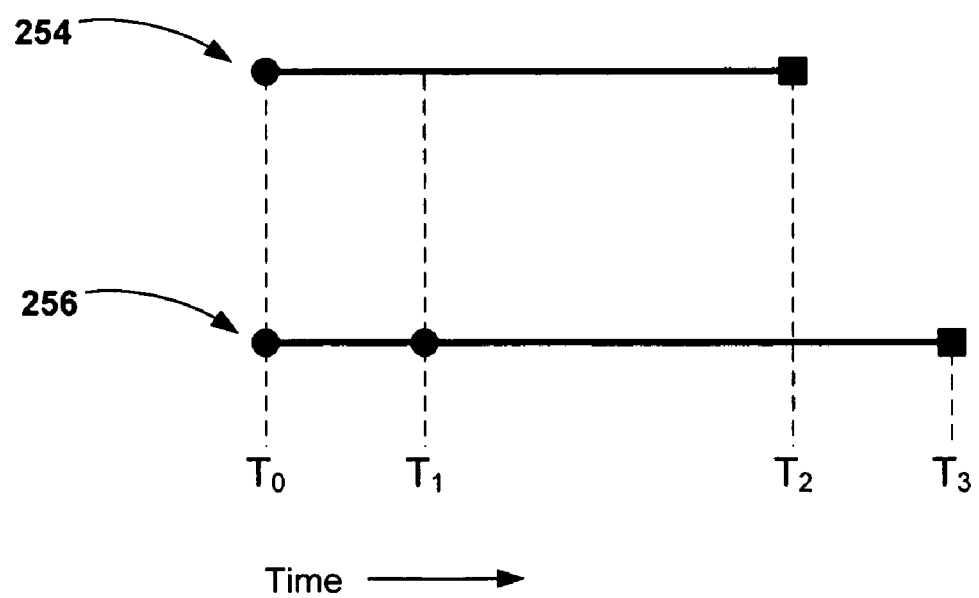
FIG. 14 is a conceptual diagram illustrating example posture search and posture stability timers with one change in posture states.

FIG. 14 is a conceptual diagram illustrating the activity of posture search timer 254 and posture stability timer 256 when one change in posture state occurs after the initiation of the timers 254, 256. As shown in FIG. 14, while patient 12 is in a first posture state, patient 12 makes an anticipatory therapy adjustment for a second, subsequent posture state that patient 12 does not currently occupy. Posture search timer 254 and posture stability timer 256 start at time $T_0$ when patient 12 makes a therapy adjustment in a first posture state occupied at time $T_0$. At time $T_1$, patient 12 changes to a second posture state that is different than the first posture state occupied at time $T_0$. Therefore, posture stability timer 256 restarts at time $T_1$, which falls within the search duration of posture search timer 254.

Time $T_2$ indicates the end of posture search timer 254. Consequently, the only posture state that processor 80 of IMD 14 will associate with the therapy adjustment is the second posture state as long as the second posture state satisfies the stability period of posture stability timer 256. At time $T_3$, patient 12 is still in the second posture when the stability period ends. Thus, the therapy adjustment is associated with the second posture state because the stability period overlapped with the search period.

It should be noted that patient 12 may make additional therapy adjustments within the search period defined by posture search timer 254. If this occurs, any previous therapy adjustments made before the search period or stability period is completed are not associated with any posture state. Therefore, both the search period and stability period must lapse in order for a therapy adjustment to be associated with a posture state. However, in some examples, processor 80 associates a therapy adjustment with a posture state as long as the search period has lapsed (i.e., posture search timer 254 has expired) or no different posture state was sensed during the search period.

Figure 15:
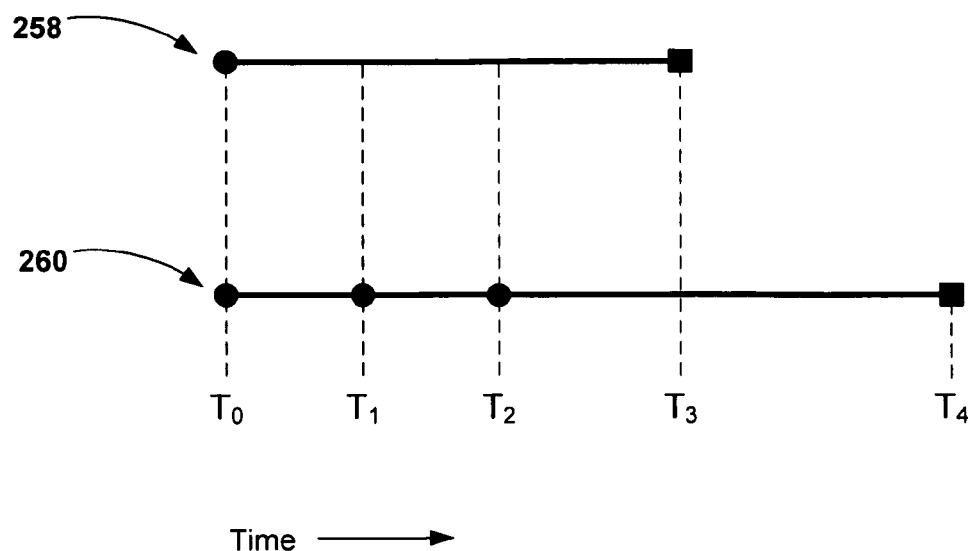
FIG. 15 is a conceptual diagram illustrating example posture search and posture stability timers with two changes in posture states.

FIG. 15 is a conceptual diagram illustrating the activity of posture search timer 258 and posture stability timer 260 when two changes in posture state occurs after the initiation of the timers 258, 260. As shown in FIG. 15, patient 12 makes an anticipatory therapy adjustment but is engaged in an interim posture state before settling into the final posture state. Posture search timer 258 and posture stability timer 260 both start at time $T_0$ when patient 12 makes the therapy adjustment while in a first (e.g., current) sensed posture state at time $T_0$. At time $T_1$, patient 12 changes to a second posture state, or an interim posture state, that is different than the initial posture state engaged at time $T_0$. Therefore, posture stability timer 260 restarts at time $T_1$, which still occurs within the search duration defined by posture search timer 258. Posture search timer 262 does not restart because an additional therapy adjustment was not made at time $T_1$.

At time $T_2$, patient 12 changes to a third posture state, and posture stability timer 260 restarts again. Again, posture search timer 262 does not restart because an additional therapy adjustment was not made at time $T_2$. Time $T_3$ coincides with the expiration of posture search timer 258, such that the only posture state processor 80 of IMD 14 will associate with the therapy adjustment is the third posture state, which patient 12 initiated at time $T_2$, as long as the third posture state satisfies the stability period of posture stability timer 260. In the example shown in FIG. 15, patient 12 is still in the third posture state at time $T_4$ when the stability period ends. As a result, processor 80 associates the therapy adjustment made at time $T_0$ with the third and final posture state because the stability period of the third posture state overlapped with the search period.

Figure 16:
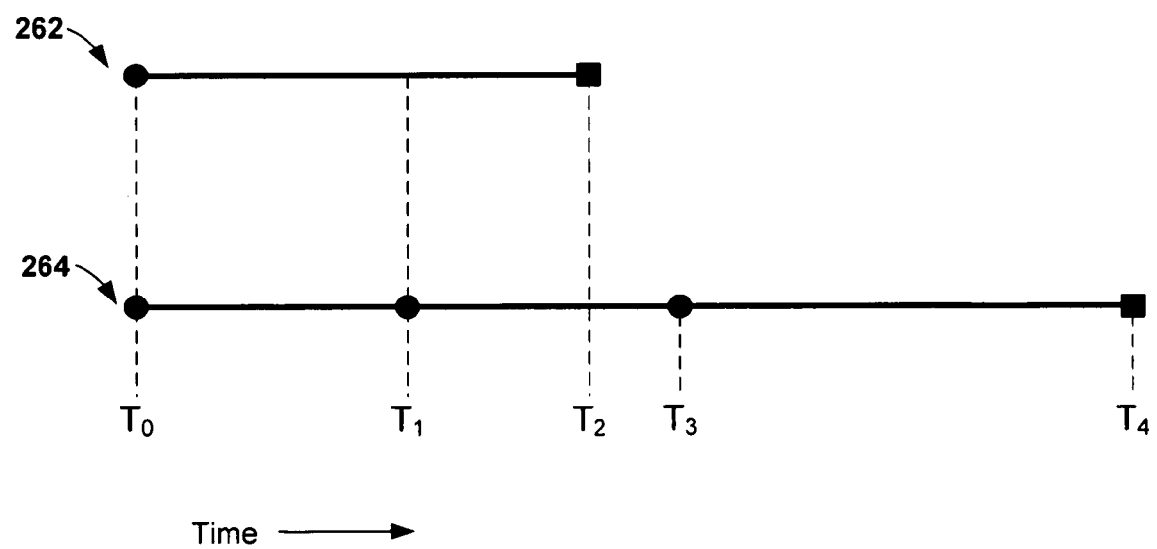
FIG. 16 is a conceptual diagram illustrating example posture search and posture stability timers with the last posture state change occurring outside of the posture search timer.

FIG. 16 is a conceptual diagram illustrating example search timer 262 and posture stability timer 264 when a final posture state change undertaken by patient 12 occurs outside of the posture search timer. As shown in FIG. 16, patient 12 makes an anticipatory therapy adjustment, but is engaged in an interim posture state for too long before settling into the final posture state for the therapy adjustment to be associated with any posture state. As a result, processor 80 of IMD 14 does not associate the therapy adjustment with any posture state in memory 82 of IMD 14 and no stability indication is associated with the final posture state. Posture search timer 262 and posture stability timer 264 both start at time $T_0$ when patient 12 makes a therapy adjustment while in a first posture state. At time $T_1$, patient 12 transitions to a second posture state, or an interim posture state, that is different than the first posture state engaged at time $T_0$. Therefore, posture stability timer 264 restarts at time $T_1$, which is still within the search duration of posture search timer 262. Posture search timer 262 does not restart because an additional therapy adjustment was not made at time $T_1$.

However, the search timer expires at time $T_2$, which is before patient 12 changes to a third posture state at time $T_3$, when posture stability timer 264 again restarts. The stability period for the third posture state then expires at time $T_4$. Because the third posture state did not start before the search period expired at time $T_2$, the search period and stability period defined by timers 262, 264, respectively, do not overlap and processor 80 does not associate the therapy adjustment made by patient 12 at time $T_0$ with any posture state. As a result, processor 80 does not update the therapy parameter values for the posture states related to the third posture state, nor does processor 80 associate the third posture state with a stability indication. The failure of the stability and search time periods to overlap indicates to processor 80 that patient 12 did not intend for the therapy adjustment to be associated with the third posture state, and, therefore, may indicate that patient 12 did not intend for the therapy adjustment to be associated with the third posture state.

In other examples, therapy adjustments may be associated with the posture state occupied at time $T_0$ when the search period and last stability period do not overlap.

The following is a further illustration of the example described in FIG. 16 to put the example in context of a patient scenario. Patient 12 may be engaged in an upright posture state when patient 12 makes the therapy adjustment at time $T_0$. In this example, the search duration is three minutes and the stability duration is also three minutes. After two minutes, or at time $T_1$, patient 12 transitions to the lying left posture, which causes processor 80 of IMD 14 to restart posture stability timer 260. If patient 12 remains within the lying left posture for the full three minutes of the stability duration, processor 80 will associate the therapy adjustment with the lying left posture. However, in the situation shown in FIG. 16, patient 12 transitions from lying left posture after only two minutes, at time $T_3$, which happens after the posture search period. At this point the therapy amplitude made at time $T_0$, will not be associated for the next posture state of patient 12. Therefore, the next posture state may be the lying back posture state. Once IMD 14 senses the lying back posture state, IMD 14 may change therapy according to the therapy parameters associated with the lying back posture because IMD 14 is operating in the automatic posture response mode. No new associations with the therapy adjustment would be made in the example of FIG. 16.

Figure 17:
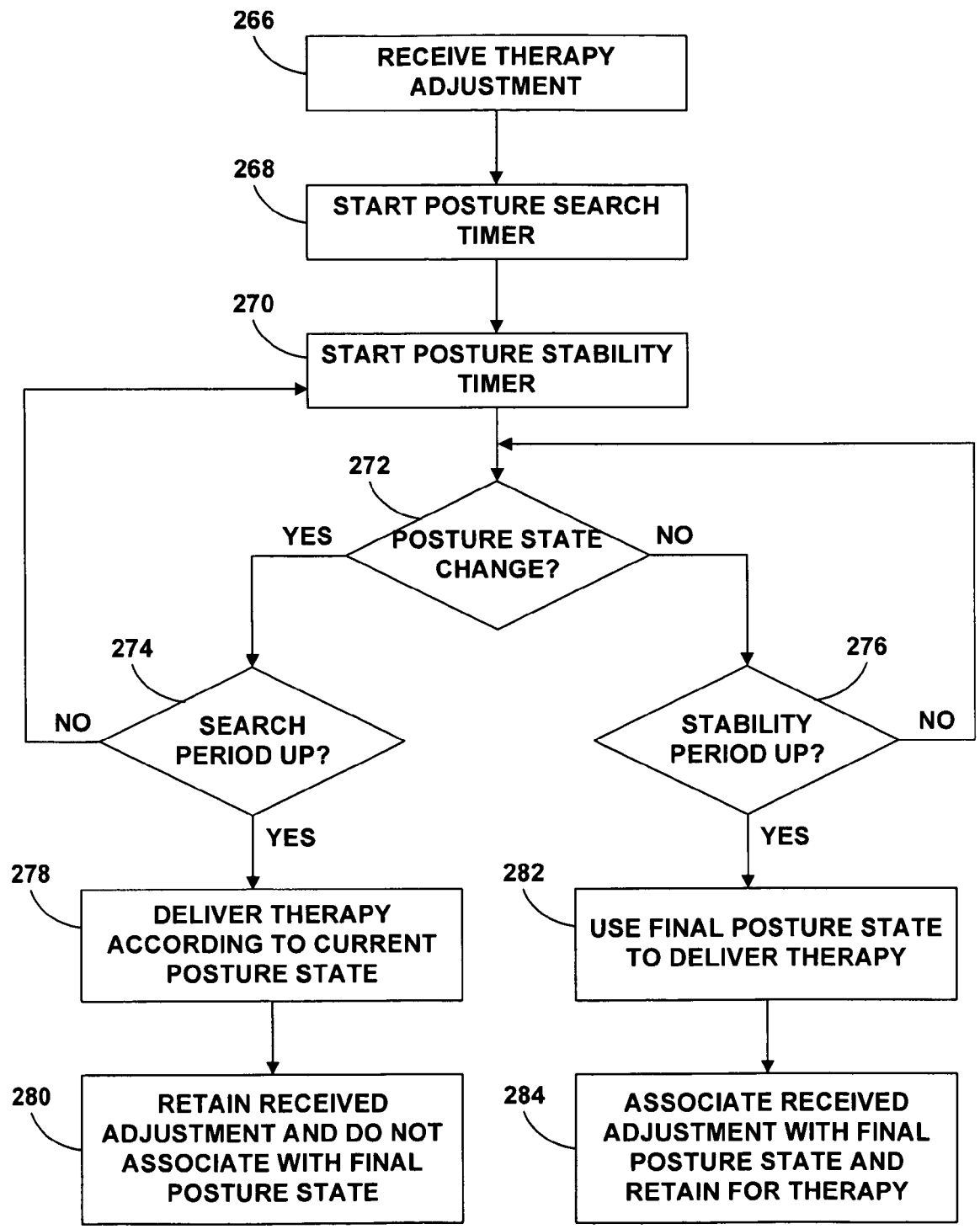
FIG. 17 is a flow diagram illustrating an example technique for associating a received therapy adjustment with a posture state.

FIG. 17 is a flow diagram illustrating an example technique for associating a therapy adjustment received from patient 12 with a posture state. Although the example of FIG. 17 will be described with respect to patient programmer 30 and IMD 14, the technique may be employed in any external programmer 20 and IMD or other computing device. As shown in FIG. 17, user interface 106 receives the therapy adjustment from patient 12 (266) and processor 80 of IMD 14 immediately starts the posture search timer (268) and the posture stability timer (270). If the posture state of patient 12 does not change (272), processor 80 checks to determine if the stability period, indicated by the posture stability timer, has expired (276). If the stability period has not expired (276), processor 80 continues to sense for a posture state change (272). Processor 80 may sense a posture state change based on information from posture state sensor 86 (FIG. 4) of IMD 14. If the stability timer has expired, indicating the search period has ended (276), processor 80 uses the final posture state, i.e., the currently sensed posture state, to deliver therapy (282). Processor 80 also associates the therapy adjustment with the final posture state and retains the therapy adjustment for future posture responsive therapy delivery (284).

If processor 80 senses a posture state change (272), processor 80 determines whether the search period, as indicated by the posture search timer, has expired (274). If the search period has not expired (274), processor 80 restarts the posture stability timer (270). If the search period has expired (274), processor 80 delivers therapy to patient 12 according to the current posture state (278). Processor 80 retains the therapy adjustment and does not associate the therapy adjustment with the final posture state because the search period did not overlap with the stability period (280).

It should be noted that processor 80 does not change therapy delivery to patient 12 until the stability period indicated by the posture stability timer expires. In other words, the posture stability timer may run independently of the posture search timer to track posture states independently of therapy adjustments. Therefore, IMD 14 may not perform any automatic posture responsive stimulation based on a posture state sensed by posture state module 86 until the posture state of patient 12 is stable and the stability period has expired. In this manner, patient 12 may not be subjected to rapidly changing therapy when transitioning between multiple posture states. Alternatively, IMD 14 may employ a separate posture stability timer for changing therapy during automatic posture response from the therapy adjustment related posture stability timer described herein.

Figure 18:
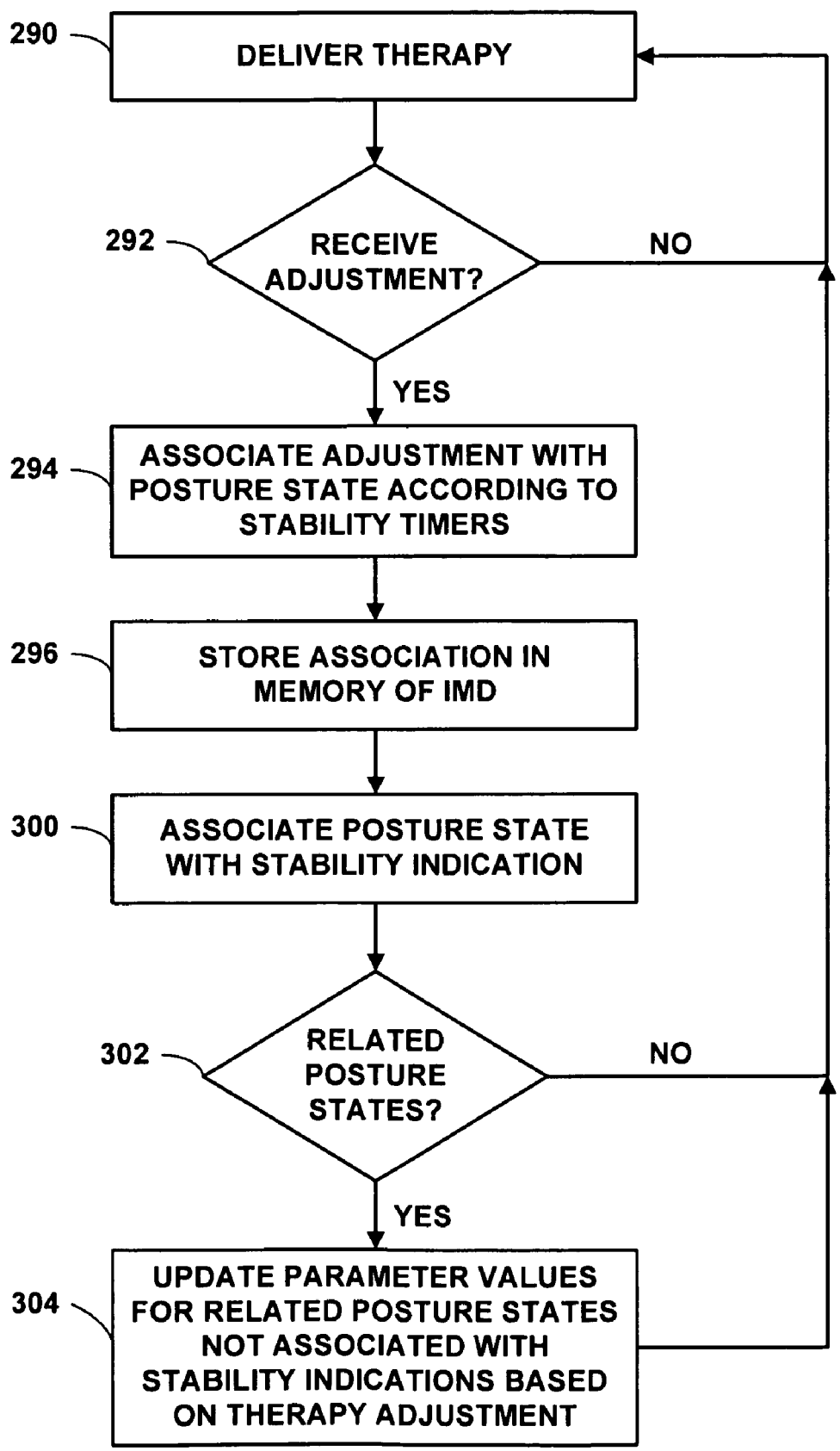
FIG. 18 is a flow diagram illustrating an example technique for associating a received therapy adjustment with a posture state and updating therapy parameter values for related posture states based on the therapy adjustment.

FIG. 18 is a flow diagram illustrating an example technique processor 80 may implement to associate therapy adjustments with posture states during a record mode of IMD 14, and to update related posture states based on a therapy adjustment. Prior to the use of the technique shown in FIG. 18, a clinician may, with the aid of clinician programmer 60, orient the posture state sensor of posture state module 86 (FIG. 4) of IMD 14 to define a plurality of posture states of patient 12, as described with respect to FIGS. 11 and 12. In addition, with some IMDs, the clinician may, with the aid of clinician programmer 60, activate a posture state record mode of IMD 14, during which processor 80 of IMD 14 associates therapy adjustments made by patient 12 with a sensed posture state. After the clinician programs IMD 14, IMD 14 delivers therapy to patient 12 according to the therapy parameter values, which may be stored as therapy programs in memory 82 (FIG. 4) of IMD 14 (290).

If IMD 14 does not receive a therapy adjustment from patient 12 via patient programmer 30 (292), processor 80 continues to control stimulation generator 84 (FIG. 4) to generate and deliver therapy to patient 12 according to the therapy programs stored in memory 82, which are selected based on a patient posture sensed via posture state module 86 (290). However, if processor 80 of IMD 14 receives a therapy adjustment from patient 12 via patient programmer 30 or another device (292), processor 80 associates the therapy adjustment with the appropriate posture state as determined by the posture search timer and the posture stability timer (294). The appropriate posture state may be determined with the aid of the posture search timer and the posture stability time, e.g., using the technique described with respect to FIG. 17.

Processor 80 stores the association between the therapy parameter adjustment and posture state in memory 82 of IMD 14 (296). The stored association may be retrieved by external programmer 20 for viewing by a user, such as a clinician, e.g., for use in analysis of therapeutic efficacy and programming of the IMD. Alternatively, patient programmer 30 may perform the associations and/or store the associations instead of IMD 14. A clinician programmer 60 may retrieve the associations from patient programmer 30.

After storing the association between the therapy adjustment and a posture state in memory 82 (296), processor 80 associates the posture state with a stability indication (300). As previously described, the stability indication may be a value, flag, signal or any other marker that can be stored in memory 82 to indicate patient 12 provided a therapy adjustment specific to the posture state. An example data structure that associates stability indications with posture states is described with reference to FIGS. 19A-19C.

In accordance with the technique shown in FIG. 18, processor 80 determines whether there are posture states related to the posture state associated with the therapy adjustment (302). In some examples, processor 80 references a data structure or other information stored in memory 82 (FIG. 4) of IMD 14 to determine whether the sensed posture state is associated with other posture states. Example data structures grouping related posture states together are described with reference to FIGS. 19A-19C. If there are no posture states related to the posture state associated with the therapy adjustment, processor 80 may continue delivering therapy according to the stored therapy programs (290), which reflects the most recent therapy adjustment provided by patient 12.

On the other hand, if there are related posture states, processor 80 updates the therapy parameter values for the related posture states based on the therapy adjustment (304). In particular, processor 80 modifies the therapy parameter values for the related posture states that are not associated with stability indications. As previously indicated, IMD 14 delivers therapy to patient 12 based on various, floating therapy parameter values when patient 12 occupies posture states that are not associated with stability indications. The therapy parameter values "float" in the sense that they are not fixed and vary based on therapy adjustments provided by patient 12 for at least one related posture state. In this way, the therapy parameter values for posture states not associated with stability indications may float to another value when patient 12 provides a therapy adjustment for a related posture state.

In some examples, processor 80 updates the therapy parameter values for the related posture states by applying the most recent therapy adjustment to the therapy parameter values. For example, processor 80 can update the therapy parameter values associated with related patient posture states such that the values are identically or substantially equal to the therapy parameter value adjusted in response to the therapy adjustment provided by patient 12. As another example, if the therapy adjustment indicates a net increase or decrease in the therapy parameter value for the sensed posture state, processor 80 can increase or decrease the therapy parameter values for the related posture states (which are not associated with stability indications) in the same manner.

In yet other examples, if more than one related posture state is associated with a stability indication, processor 80 sets the therapy parameter values associated with related patient posture states that are not associated with stability indications at values substantially equal to the lowest, highest, or average value of the therapy parameter values associated with posture states associated with a stability indication. A clinician may predetermine whether a particular posture state group is updated based on the lowest, highest, or average value of the therapy parameter values associated with posture states associated with a stability indication.

During operation of therapy system 10, processor 80 selects one of the lowest, highest, or average value of the therapy parameter values based on the specific group of related posture states or based on a clinician selected value. For example, in some examples in which the related posture states are lying posture states, processor 80 selects the lowest or average value of the therapy parameter values associated with posture states associated with a stability indication. As discussed above, when patient 12 is in a lying posture state, leads 16 (FIG. 1A) may be compressed toward a stimulation site, which may result in an increased intensity of therapy delivery. Selecting a lowest or average value of the therapy parameter values associated with lying posture states associated with a stability indication may help decrease the possibility of delivering uncomfortable stimulation to patient 12 to the relative position of electrodes of leads 16 and the target tissue site.

In some examples in which the related posture states are upright posture states, processor 80 selects the highest or average value of the therapy parameter values associated with posture states associated with a stability indication. Selecting a highest or average value of the therapy parameter values associated with upright posture states associated with a stability indication may help decrease the possibility that insufficient therapy will be delivered to patient 12. That is, selecting a highest or average value of the therapy parameter values associated with upright posture states associated with a stability indication helps maintain a therapeutic level of therapy.

After updating the therapy parameter values for the related posture states (304), processor 80 continues delivering posture responsive therapy (290) with the updated therapy parameter values. In addition, after each posture state in a group of related posture states is associated with a stability indication, processor 80 may stop the automatic association of one therapy adjustment to multiple posture states based on a therapy adjustment for one posture state. While patient 12 may continue making therapy adjustments for a specific posture state, processor 80 may only update a sensed posture state with the therapy adjustment. In some cases, the clinician or IMD 14 automatically resets the stability indications, e.g., when posture state definitions stored by IMD 14 are updated, such that the posture states are not associated with stability indications until patient 12 subsequently provides a therapy adjustment for the specific posture states.

FIGS. 19A-19C illustrate an example data structure 310 that associates patient posture states with stability indications and therapy parameter values. Memory 82 of IMD 14 can store data structure 310. In other examples, data structure 310 can be stored by a memory of another device, such as programmer 20. Moreover, although tables are shown in FIGS. 19A-19C, data structures indicating related patient posture states and respective stability indications and therapy parameter values can take any suitable form. In some examples, user interface 106 (FIG. 6) of programmer 20 or a user interface of another device presents data structure 310 to a user (e.g., a clinician or patient 12) in order to present information identifying related posture states and posture states for which patient 12 has not provided a therapy adjustment (as indicated by an associated stability indication or lack thereof).

IMD 14 stores any suitable number of posture state groups, such as two or more posture state groups. Data structure 310 includes the posture states of one group of related posture states, which is labeled Posture State Group A. In the example shown in FIGS. 19A-19C, the lying front, lying back, lying left, and lying right posture states are grouped together as being related. As previously indicated, the posture states in a particular group are selected by a clinician or are automatically selected by IMD 14 or programmer 20 based on characteristics of the therapy parameter values associated with each of the posture states, patient symptoms or condition in each of the posture states, and/or the posture state definitions.

Data structure 310 includes posture state column 312 that indicates a posture state, stability indication column 314 that indicates whether the respective posture state is associated with a stability indication, and therapy parameter value column 316 that provides the therapy parameter value associated with the respective posture state. Although only one therapy parameter value column 316 is shown in FIGS. 19A-19C, in other examples, more than one therapy parameter value may be associated with each posture state. In FIGS. 19A-19C, the therapy parameter value is a voltage amplitude. In other examples, data structure 310 may also associate a current amplitude, frequency, electrode combination, or other stimulation parameter values with each posture state. In addition, in examples in which the IMD provides another type of therapy, such as drug delivery, therapy parameter value column 316 defines values for other types of therapy parameters.

Stability indication column 314 provides a binary indication of whether a posture state is associated with a stability indication. A "1" indicates a stability indication has been generated and associated with the posture state, and a "0" indicates that a stability indication is not associated with the posture state. Data structure 310 shown in FIG. 19A reflects a situation in which the lying front posture state is associated with a stability indication (as indicated by the binary "1"). Thus, patient 12 has provided input indicating a therapy adjustment when patient 12 occupied the lying front posture state or prior to occupying the lying front posture state. In the example shown in FIG. 19A, the therapy adjustment provided by patient 12 resulted in an amplitude value of 2.2 volts (V). For example, patient 12 may specify the exact amplitude value of 2.2 V or may increase or decrease a previously selected therapy parameter value to 2.2 V.

Upon receiving the therapy adjustment for the lying front posture state, processor 80 of IMD 14 updates the therapy parameter value of the lying front posture state. In addition, for each of the related posture states not associated with a stability indication, processor 80 updates the therapy parameter values based on the therapy adjustment. In the example shown in FIG. 19A, the lying back, lying left, and lying right posture states are not associated with stability indications. Thus, in the example shown in FIG. 19A, processor 80 updates the therapy parameter values associated with the lying back, lying left, and lying right posture states to substantially equal the therapy parameter value associated with the lying front posture state. As indicated above with respect to FIG. 18, other types of updates are contemplated.

FIG. 19B reflects an updated data structure 310 after patient 12 provides a therapy adjustment that is associated with the lying back posture state, e.g., using the technique shown in FIG. 17. Because patient 12 provided a therapy adjustment specific to the lying back posture state, processor 80 has generated and stored a stability indication for the lying back posture state, as indicated by the binary "1" in column 314. The therapy parameter value for the lying back posture state is 3.8 V following the therapy adjustment.

Upon receiving the therapy adjustment for the lying back posture state, processor 80 updates the therapy parameter value of the lying back posture state and the parameter values for each of the related posture states not associated with a stability indication. In the example shown in FIG. 19B, the lying left and lying right posture states are not associated with stability indications, whereas the lying front posture state is associated with a stability indication. Thus, processor 80 does not update the therapy parameter value associated with the lying front posture state based on the therapy adjustment specific to the lying back posture state. Processor 80 does, however, update the therapy parameter values associated with the lying left and lying right posture states based on the therapy adjustment specific to the lying back posture state.

In the example shown in FIG. 19B, processor 80 sets the therapy parameter values associated with the lying left and lying right posture states at the lowest therapy parameter value associated with stability indications. In particular, in the example shown in FIG. 19B, processor 80 sets the therapy parameter values associated with the lying left and lying right posture states at 2.2 V, which the therapy parameter value associated with the lying front posture state. In other examples, processor 80 sets the therapy parameter values associated with the lying left and lying right posture states at the highest therapy parameter value associated with stability indications, which would be 3.8 V in the example shown in FIG. 19B, or at the average value of the therapy parameter values associated with stability indications, which would be 3.0 V. In yet other examples, processor 80 sets the therapy parameter values associated with the lying left and lying right posture states at the most recently adjust therapy parameter value, which would be 3.8 V in the example shown in FIG. 19B.

FIG. 19C reflects an updated data structure 310 after patient 12 provides a therapy adjustment that is associated with the lying right posture state, e.g., using the technique shown in FIG. 17. Because patient 12 provided a therapy adjustment specific to the lying right posture state, processor 80 has generated and stored a stability indication for the lying right posture state, as indicated by the binary "1" in column 314. The therapy parameter value for the lying right posture state is 2.1 V following the therapy adjustment.

After updating the therapy parameter value for the lying right posture state in response to the therapy adjustment provided by patient 12, processor 80 updates the parameter values for each of the related posture states not associated with a stability indication. In the example shown in FIG. 19C, the lying left posture state is not associated with a stability indication, whereas the lying front and lying back posture states are associated with stability indications. Thus, processor 80 does not update the therapy parameter values associated with the lying front and lying back posture states based on the therapy adjustment specific to the lying right posture state. Processor 80 does, however, update the therapy parameter value associated with the lying left posture state based on the therapy adjustment specific to the lying right posture state.

In the example shown in FIG. 19C, processor 80 sets the therapy parameter value associated with the lying left posture state at the lowest therapy parameter value associated with stability indications. In particular, in the example shown in FIG. 19C, processor 80 sets the therapy parameter value associated with the lying left posture state at 2.1 V, which is the therapy parameter value associated with the lying right posture state. Other therapy parameter adjustments are contemplated, as described with respect to FIG. 19C.

As previously indicated, in some examples, processor 80 of IMD 14, processor 92 of programmer 26, processor 104 of programmer 20 or a processor of another device may update the therapy parameter values of a plurality of stored posture states in order to maintain a predetermined ratiometric balance between the therapy parameter values of the different patient posture states upon receiving an adjustment to a related or unrelated posture state. Programmer 20 may, for example, present a user interface that presents a plurality of posture states and/or the different programs and the different ratiometric balances between the therapy parameter values (e.g., the amplitude values) associated with the different posture states. The ratiometric balances may be presented graphically (e.g., bar graphs that have relative lengths that represent the relative proportion of the amplitudes of each of the therapy programs).

In some examples, upon patient 12 or another user may provide input via programmer 20 change one therapy parameter value, and a processor of IMD 14 or programmer 20 applies the adjustment as a global adjustment to each of the other therapy parameter values for the other therapy programs and/or posture states in order to maintain the ratiometric balance.

An example technique for applying a single request for a global adjustment to a therapy parameter value of a therapy program to a plurality of therapy programs is described in commonly-assigned U.S. Pat. No. 7,489,970 to Lee et al., which is entitled, "MANAGEMENT OF NEUROSTIMULATION THERAPY USING PARAMETER SETS" and issued on Feb. 10, 2009, and commonly-assigned U.S. patent application Ser. No. 11/372,354 to Nolan et al., which is entitled, "GLOBAL PARAMETER ADJUSTMENT FOR MULTIPLE STIMULATION PROGRAMS" and was filed on Mar. 9, 2006. U.S. Pat. No. 7,489,970 to Lee et al. and U.S. patent application Ser. No. 11/372,354 to Nolan et al. are incorporated herein by reference in their entireties.

As described in U.S. patent application Ser. No. 11/372,354 to Nolan et al., in one technique for making a global adjustment to a plurality of therapy programs, each program may have a predetermined step value, a step value calculated based upon a remaining possible adjustment range, or a step value calculated for each stimulation program to keep parameter ratios equal between the plurality of stimulation programs during the global adjustment. Processor 80 of IMD 14, processor 92 of programmer 26, processor 104 of programmer 20 or a processor of another device may make an adjustment to a plurality of therapy programs associated with a respective posture state using the step values discussed in U.S. patent application Ser. No. 11/372,354 to Nolan et al.

A global adjustment (or a "multi-program adjustment) eliminates the need for patient 12 to manually adjust the amplitude for each individual stimulation program. Instead, multi-program adjustment permits a global adjustment of a parameter or parameters across multiple programs. As described in U.S. patent application Ser. No. 11/372,354 to Nolan et al., although a single parameter adjustment results in a multi-program adjustment of the parameter, the actual magnitude of the adjustment may be different for different programs. In particular, the magnitude of the adjustment may be different in each stimulation program to maintain current or predefined amplitude ratios between the programs. Therefore, the global adjustment may not only reduce multiple steps of programming for the patient, but also promote uniformity and reduce patient error that could result when modifying several programs with varying parameter values.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry. In examples in which information is processed and presented to a user (e.g., patient 12 or a clinician), the information may be processed and/or presented via a patient or clinician programmer or a computer that communicates with the patient programmer or clinician programmer.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Many examples have been described. Various modifications may be made without departing from the scope of the claims. These and other examples are within the scope of the following claims.

The invention claimed is:

1. A method comprising:
receiving user input indicating an adjustment to a first therapy parameter value that defines therapy delivered to a patient by a medical device;
associating the adjustment with a sensed posture state of the patient;
associating the sensed posture state with a stability indication that indicates the user has inputted the adjustment specific to the sensed posture state, and storing the stability indication within a memory; and
based on the adjustment, automatically updating a second therapy parameter value associated with at least one patient posture state related to the sensed posture state and not associated with a respective stability indication.

2. The method of claim 1, wherein an absence of an association between the at least one patient posture state related to the sensed postured state and a respective stability indication indicates the user has not inputted an adjustment specific to the at least one patient posture state related to the sensed posture state.

3. The method of claim 1, further comprising:
starting a posture search timer having a search period upon receiving the user input; and
starting a posture stability timer having a stability period, wherein associating the adjustment with the sensed posture state occurs only when the sensed posture state begins within the search period and does not change during the stability period.

4. The method of claim 3, wherein the search period is between about thirty seconds and about thirty minutes and the stability period is between about thirty seconds and about thirty minutes.

5. The method of claim 3, wherein the search period is about three minutes and the stability period is about three minutes.

6. The method of claim 1, wherein the adjustment to the first therapy parameter value indicates a net change to the first therapy parameter value, and updating the second therapy parameter value comprises adjusting the second therapy parameter value based on the net change.

7. The method of claim 6, wherein updating the second therapy parameter value comprises adjusting the second therapy parameter value based on the net change comprises updating the second therapy parameter value to maintain a predetermined ratiometric balance between the first and second therapy parameter values.

8. The method of claim 1, wherein updating the second therapy parameter value comprises adjusting the second therapy parameter value to be substantially equal to the first therapy parameter value.

9. The method of claim 1, wherein updating the second therapy parameter value comprises:
determining a lowest, highest or average therapy parameter value of a group of therapy parameter values associated with the related posture states and associated with stability indications in a memory; and
updating the second therapy parameter value based on the lowest, highest or average therapy parameter value.

10. The method of claim 9, wherein the related posture states comprise related lying posture states and determining the lowest, highest or average therapy parameter value of a group of therapy parameter values comprises determining the lowest or average therapy parameter value, and updating the second therapy parameter value based on the lowest, highest or average therapy parameter value comprises updating the second therapy parameter value based on the lowest or average therapy parameter value.

11. The method of claim 9, wherein the related posture states comprise related upright posture states and determining the lowest, highest or average therapy parameter value of a group of therapy parameter values comprises determining the highest or average therapy parameter value, and updating the second therapy parameter value based on the lowest, highest or average therapy parameter value comprises updating the second therapy parameter value based on the highest or average therapy parameter value.

12. The method of claim 1, further comprising storing the adjustment and the sensed posture state in a memory.

13. The method of claim 12, further comprising associating the sensed posture state with the at least one posture state related to the sensed posture state.

14. The method of claim 13, wherein the sensed posture state comprises a first lying posture state and the at least one posture state related to the sensed posture state comprises a second lying posture state.

15. The method of claim 13, wherein the sensed posture state comprises one of an upright posture state or an upright and active posture state, and the at least one posture state related to the sensed posture state comprises another upright posture or upright and active posture state.

16. The method of claim 1, further comprising determining the at least one patient posture state related to the sensed posture state by at least determining whether any posture states stored in a memory are associated with similar posture state definitions, similar therapy parameter values or similar patient conditions.

17. The method of claim 1, further comprising receiving input via a user interface of a medical device programmer that indicates the at least one patient posture state that is related to the sensed posture state.

18. A system comprising:
a posture state sensor that generates a signal indicative of a patient posture state;
a user input mechanism that receives user input indicating an adjustment to a first therapy parameter value that defines therapy delivered to a patient; and
a processor that associates the adjustment with a sensed posture state of the patient determined based on the signal from the posture state sensor, associates the sensed posture state with a stability indication that indicates the user has inputted the adjustment specific to the sensed posture state, and based on the adjustment, updates a second therapy parameter value associated with at least one patient posture state related to the sensed posture state and not associated with a respective stability indication.

19. The system of claim 18, further comprising a memory, wherein the processor stores the adjustment, the stability indication, and the sensed posture state in the memory.

20. The system of claim 18, wherein an absence of an association between the at least one patient posture state related to the sensed postured state and a respective stability indication indicates the user has not inputted an adjustment specific to the at least one patient posture state related to the sensed posture state.

21. The system of claim 18, wherein the processor starts a posture search timer having a search period upon receiving the user input, and starts a posture stability timer having a stability period, and wherein the processor associates the adjustment with the sensed posture state only when the sensed posture state begins within the search period and does not change during the stability period.

22. The system of claim 21, wherein the search period is between about thirty seconds and about thirty minutes and the stability period is between about thirty seconds and about five minutes.

23. The system of claim 18, wherein the adjustment to the first therapy parameter value indicates a net change to the first therapy parameter value, and the processor updates the second therapy parameter value by at least adjusting the second therapy parameter value by the net change.

24. The system of claim 18, wherein the processor updates the second therapy parameter value by at least adjusting the second therapy parameter value to be substantially equal to the first therapy parameter value.

25. The system of claim 18, wherein the processor updates the second therapy parameter value by at least determining a lowest, highest or average therapy parameter value of a group of therapy parameter values associated with the related posture states and associated with stability indications in the memory, and updating the second therapy parameter value based on the lowest, highest or average therapy parameter value.

26. The system of claim 25, wherein the related posture states comprise related lying posture states and the processor determines the lowest or average therapy parameter value of the group of therapy parameter values and updates the second therapy parameter value based on the lowest or average therapy parameter value.

27. The system of claim 25, wherein the related posture states comprise related upright posture states and the processor determines the highest or average therapy parameter value of the group of therapy parameter values and updates the second therapy parameter value based on the highest or average therapy parameter value.

28. The system of claim 18, further comprising a memory, wherein the processor is configured to associate the sensed posture state with the at least one posture state related to the sensed posture state, and store the associated sensed posture state and at least one posture state related to the sensed posture state in the memory.

29. The system of claim 28, wherein the sensed posture state comprises a first lying posture state and the at least one posture state posture state related to the sensed posture state comprises a second lying posture state.

30. The system of claim 28, wherein the sensed posture state comprises one of an upright posture state or an upright and active posture state, and the at least one posture state related to the sensed posture state comprises another upright posture or upright and active posture state.

31. The system of claim 28, wherein the memory is located within at least one of an implantable medical device that delivers therapy to the patient or an external programmer that receives the therapy adjustment.

32. The system of claim 28, further comprising a user interface that receives input from a user indicating the at least one posture state related to the sensed posture state.

33. The system of claim 18, wherein the processor automatically determines the at least one patient posture state related to the sensed posture state by at least determining whether any posture states stored in the memory are associated with similar posture state definitions, similar therapy parameter values or similar patient conditions.

34. A non-transitory computer-readable medium comprising instructions that cause a programmable processor to:
receive user input indicating an adjustment to a first therapy parameter value that defines therapy delivered to a patient;
associate the adjustment with a sensed posture state of the patient;
associate the sensed posture state with a stability indication in a memory, wherein the stability indication indicates the user has inputted the adjustment specific to the sensed posture state;
based on the adjustment, update a second therapy parameter value associated with at least one patient posture state related to the sensed posture state and not associated with a respective stability indication; and
control a medical device to deliver therapy to the patient according to the adjusted first therapy parameter value and the updated second therapy parameter value.

35. The non-transitory computer-readable medium of claim 34, wherein an absence of an association between the at least one patient posture state related to the sensed postured state and a respective stability indication indicates the user has not inputted an adjustment specific to the at least one patient posture state related to the sensed posture state.

36. A system comprising:
means for receiving user input indicating an adjustment to a first therapy parameter value that defines therapy delivered to a patient;
means for associating the adjustment with a sensed posture state of the patient;
means for associating the sensed posture with a stability indication that indicates the user has inputted the adjustment specific to the sensed posture state; and means for updating a second therapy parameter value associated with at least one patient posture state related to the sensed posture state and not associated with a respective stability indication based on the adjustment.

37. The system of claim 36, wherein an absence of an association between the at least one patient posture state related to the sensed postured state and a respective stability indication indicates the user has not inputted an adjustment specific to the at least one patient posture state related to the sensed posture state.

* * * * *